US011990210B2

(12) United States Patent
Wilkie et al.

(10) Patent No.: US 11,990,210 B2
(45) Date of Patent: May 21, 2024

(54) NUTRITIONAL SUPPLEMENT BLACK SHOT MIXTURE METHOD AND APPARATUS

(71) Applicants: Louise Wilkie, Surrey, CA (US); Jacqueline Wilkie, Calabasas, CA (US)

(72) Inventors: Louise Wilkie, Surrey, CA (US); Jacqueline Wilkie, Calabasas, CA (US)

( * ) Notice: Subject to any disclaimer, the term of this patent is extended or adjusted under 35 U.S.C. 154(b) by 0 days.

(21) Appl. No.: 17/940,926

(22) Filed: Sep. 8, 2022

(65) Prior Publication Data

US 2023/0107885 A1 Apr. 6, 2023

Related U.S. Application Data

(63) Continuation of application No. 16/751,447, filed on Jan. 24, 2020, now abandoned.

(51) Int. Cl.
| | |
|---|---|
| *G16C 20/50* | (2019.01) |
| *A23L 33/10* | (2016.01) |
| *A23L 33/105* | (2016.01) |
| *A23L 33/15* | (2016.01) |
| *A23L 33/16* | (2016.01) |
| *B01J 19/08* | (2006.01) |
| *G16C 10/00* | (2019.01) |
| *G16C 20/10* | (2019.01) |
| *G16C 20/20* | (2019.01) |
| *G16C 60/00* | (2019.01) |
| *G16C 20/70* | (2019.01) |
| *G16C 20/90* | (2019.01) |

(52) U.S. Cl.
CPC .............. *G16C 20/50* (2019.02); *A23L 33/10* (2016.08); *A23L 33/105* (2016.08); *A23L 33/15* (2016.08); *A23L 33/16* (2016.08); *B01J 19/087* (2013.01); *G16C 10/00* (2019.02); *G16C 20/10* (2019.02); *G16C 20/20* (2019.02); *G16C 60/00* (2019.02); *G16C 20/70* (2019.02); *G16C 20/90* (2019.02)

(58) Field of Classification Search
CPC ........ G16C 20/50; G16C 10/00; G16C 20/20; G16C 20/90; G16C 20/70; A23L 33/10; A23L 33/105; A23L 33/16; A23L 33/15; C16C 20/10; C16C 60/00
USPC ........................................................ 422/186
See application file for complete search history.

(56) References Cited

U.S. PATENT DOCUMENTS 6,558,712 B1 * 5/2003 Ghosal ................ A61K 31/525
424/195.18

FOREIGN PATENT DOCUMENTS

WO   WO-2014171944 A1 * 10/2014   ........... A23L 1/0315

* cited by examiner

*Primary Examiner* — Hamid R Badr
(74) *Attorney, Agent, or Firm* — Edmond DeFrank

(57) ABSTRACT

The embodiments disclose a method including planning a combining sequence of the atoms and compounds with carbon atoms to achieve sequentially predetermined covalent and ion bonding molecular structures, using magnetic fields of force to align atoms and molecules to uniformly orient the atoms and molecules polar alignments when sequentially combining with the carbon atoms, confirming the final carbon combined compound molecular structure conforms to the planned sequential molecular structure using an apparatus, and creating a beverage using the final carbon combined compound molecules to fortify the beverage nutritional content including fulvic acid.

20 Claims, 24 Drawing Sheets

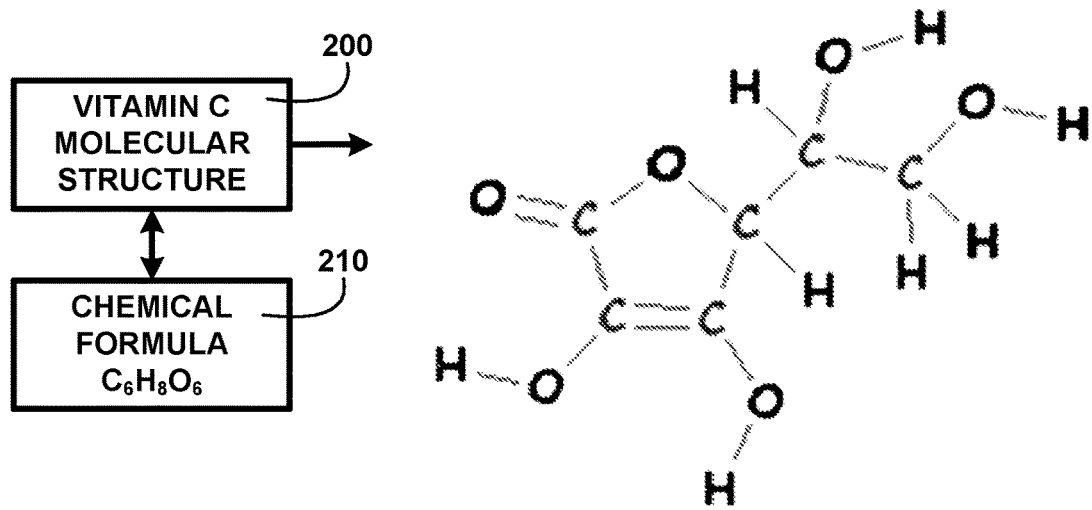
FIG. 2A
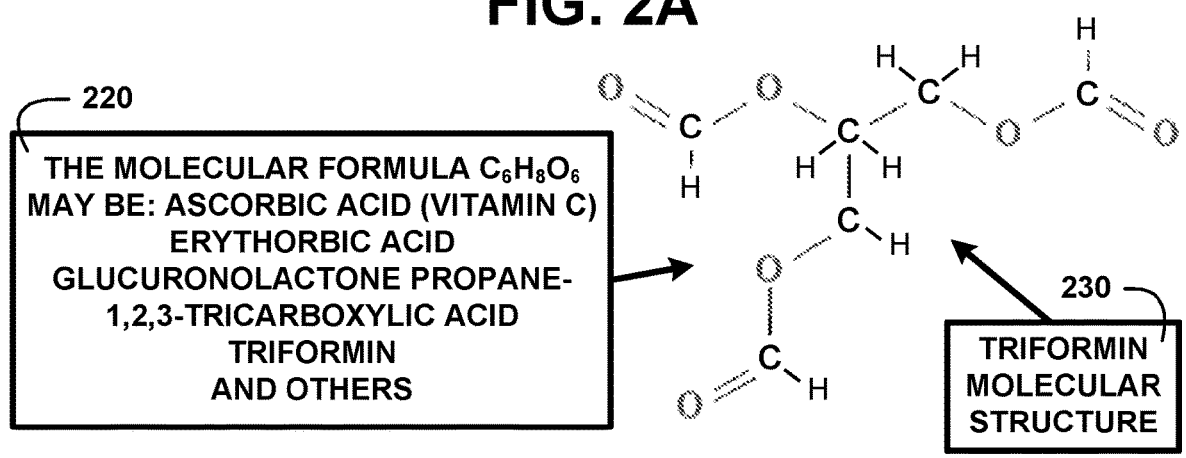
FIG. 2B
| THERE IS ALMOST NO LIMIT TO THE SIZE AND SHAPE OF MOLECULES THAT CAN BE MADE WITH CARBON ATOMS | 240 |
↓
| THE STRUCTURE OF MOLECULES FROM COMBINING ELEMENTS AND MOLECULES WITH CARBON RESULT FROM ELECTRON BINDING ENERGY | 250 |
↓
| THE ELECTRON PROPERTIES INCLUDE THE NUMBER OF ATOM ELECTRONS AND SHELL STRUCTURE, ELECTRON AFFINITY AND ELECTRONEGATIVITY | 260 |
FIG. 2C

| ACTIVATED CARBON OTHER COMMON COMPONENTS ||
|---|---|
| FORMULA | CONCENTRATION (PPM) |
| Al | 0.101 |
| Ca | 0.2053 |
| $CH_2$ | 98.6 |
| Cl | 0.0539 |
| Cr | 0.0021 |
| Cu | 0.0015 |
| Fe | 0.2322 |
| K | 0.4539 |
| Mg | 0.0252 |
| Mn | 0.0066 |
| Mo | 0.001 |
| Si | 0.0619 |

NUTRITIONAL SUPPLEMENT BLACK SHOT MIXTURE METHOD AND APPARATUS

This Patent Application is a Continuation and claims priority to United States Patent Application entitled: "CARBON HOOKS COMPOUND BONDING METHOD AND APPARATUS", U.S. Ser. No. 16/751,447 filed on Jan. 24, 2020 filed by Louise Wilkie et al., the U.S. Patent Application being incorporated herein by reference.

BACKGROUND

Most chemical manufacturing chemical processes end up with a residual waste byproduct including one or more catalyst and removed elements and fractions of the original compound that is discarded. Sometimes the discard is not handled in a proper manner to prevent contamination of soils and water sources for example rivers and subterranean aquifers.

BRIEF DESCRIPTION OF THE DRAWINGS

FIG. 2A shows for illustrative purposes only an example of vitamin c molecular structure of one embodiment.

FIG. 2B shows for illustrative purposes only an example of other c6h8o6 compounds of one embodiment.

FIG. 2C shows a block diagram of an overview of size and shape of carbon molecules of one embodiment.

DETAILED DESCRIPTION OF THE INVENTION

In a following description, reference is made to the accompanying drawings, which form a part hereof, and in which is shown by way of illustration a specific example in which the invention may be practiced. It is to be understood that other embodiments may be utilized and structural changes may be made without departing from the scope of the present invention.

General Overview:

It should be noted that the descriptions that follow, for example, in terms of carbon hooks compound bonding method and apparatus is described for illustrative purposes and the underlying system can apply to any number and multiple types of molecules. In one embodiment of the present invention, the carbon hooks compound bonding method and apparatus can be configured using permanent and electromagnets. The carbon hooks compound bonding method and apparatus can be configured to include a graphite compound and can be configured to include an activated carbon compound using the present invention.

The term used herein "carbon hooks" expresses a common phrasing to explain that each atom has hooks with which it can couple with other atoms to give rise to molecules. The term "hooks" is a common expression for atomic electrons which can form bonds with other electrons of the same atom or others. Carbon has 4 electrons (hooks) which easily form covalent and ionic bonds with other electrons.

Figure 1:
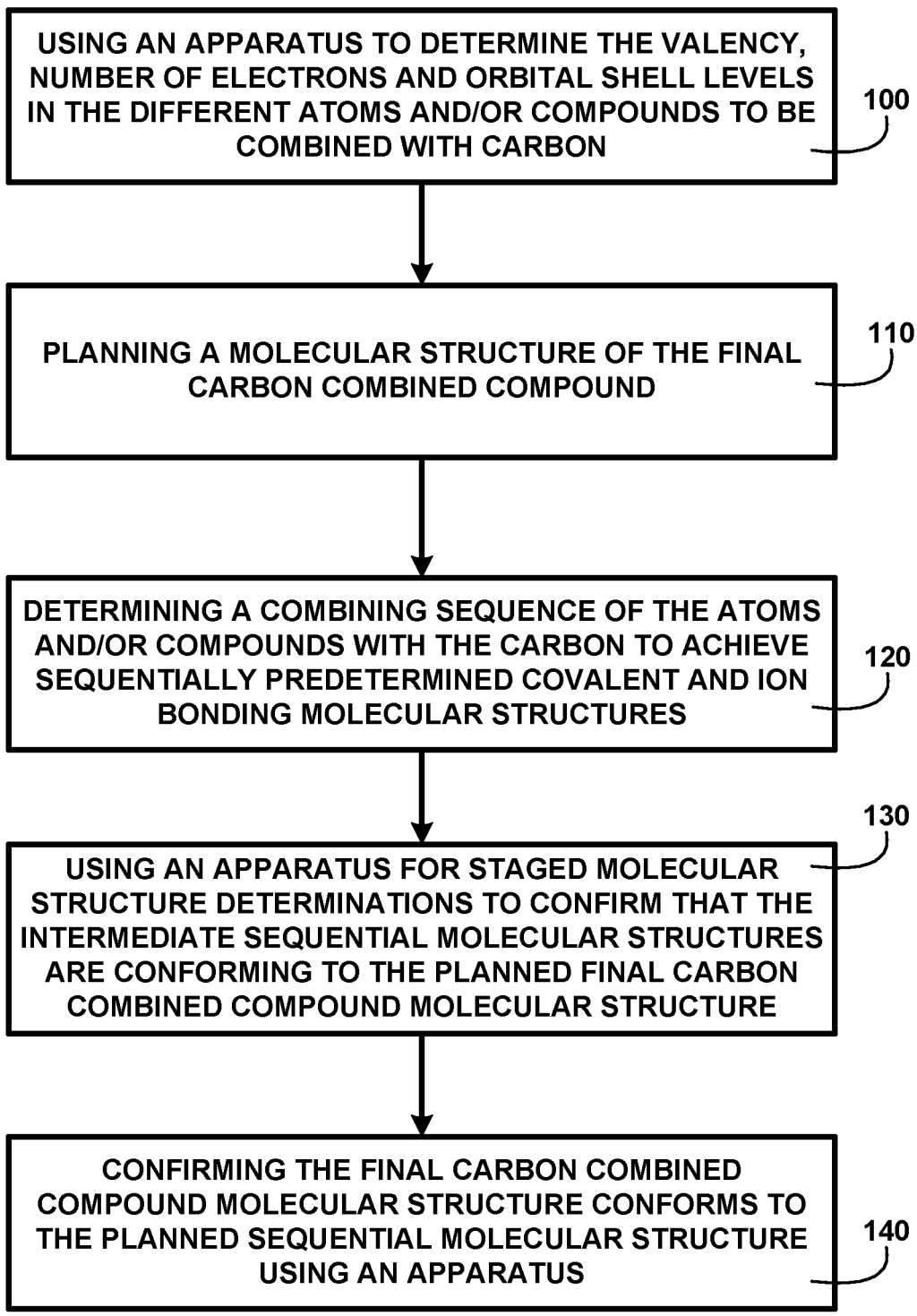
FIG. 1 shows a block diagram of an overview flow chart of a carbon hooks compound bonding method and apparatus of one embodiment.

FIG. 1 shows a block diagram of an overview flow chart of a carbon hooks compound bonding method and apparatus of one embodiment. FIG. 1 shows using an apparatus to determine the valency, number of electrons and orbital shell levels in the different atoms and/or compounds to be combined with carbon 100. The processes include planning a molecular structure of the final carbon combined compound 110.

Processing includes determining a combining sequence of the atoms and/or compounds with the carbon to achieve sequentially predetermined covalent and ion bonding molecular structures 120. Using an apparatus for staged molecular structure determinations to confirm that the intermediate sequential molecular structures are conforming to the planned final carbon combined compound molecular structure 130. Another process is for confirming the final carbon combined compound molecular structure conforms to the planned sequential molecular structure using an apparatus 140 of one embodiment.

DETAILED DESCRIPTION

FIG. 2A shows for illustrative purposes only an example of vitamin C molecular structure of one embodiment. FIG. 2A shows the vitamin C molecular structure 200 of the molecular formula $C_6H_8O_6$ 210 of one embodiment.

Other $C_6H_8O_6$ Compounds:

FIG. 2B shows for illustrative purposes only an example of other $C_6H_8O_6$ compounds of one embodiment. FIG. 2B shows the chemical formula $C_6H_8O_6$ may be: ascorbic acid (vitamin C); erythorbic acid; glucuronolactone propane-1, 2,3-tricarboxylic acid; triformin; and others 220. For example the chemical formula $C_6H_8O_6$ can take on the triformin molecular structure 230 of one embodiment.

Size and Shape of Carbon Molecules:

FIG. 2C shows a block diagram of an overview of size and shape of carbon molecules of one embodiment. FIG. 2C shows there is almost no limit to the size and shape of molecules that can be made with carbon atoms 240. The structure of molecules from combining elements and molecules with carbon result from electron binding energy 250. The electron properties include the number of atom electrons and shell structure, electron affinity and electronegativity 260 of one embodiment.

Figure 3:
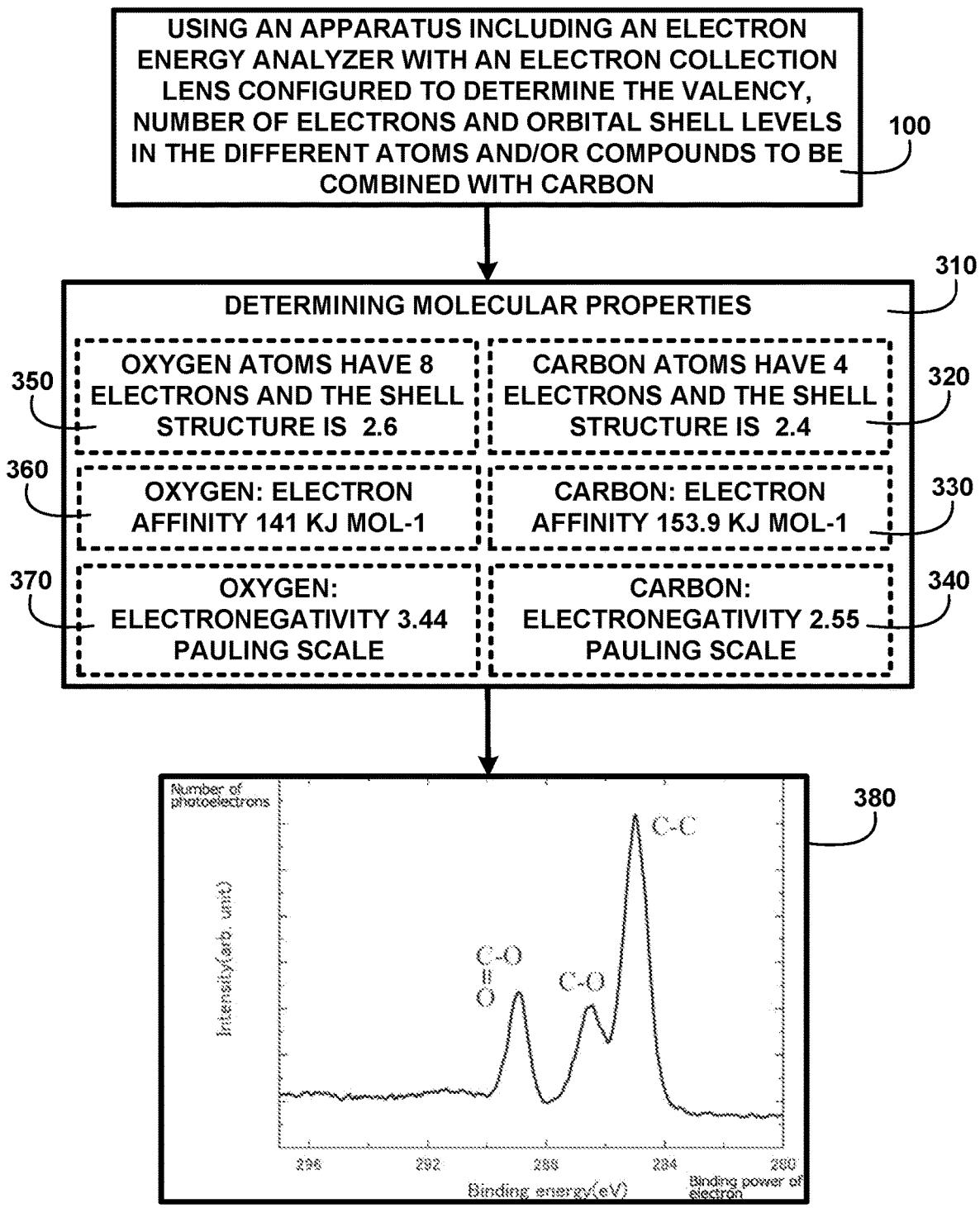
FIG. 3 shows for illustrative purposes only an example of determining molecular properties of one embodiment.

Determining Molecular Properties:

FIG. 3 shows for illustrative purposes only an example of determining molecular properties of one embodiment. FIG. 3 shows using an apparatus to determine the valency, number of electrons and orbital shell levels in the different atoms and/or compounds to be combined with carbon 100. For example determining molecular properties 310 of a compound may show carbon atoms have 6 electrons and the shell structure is 2.4 320; carbon: electron affinity 153.9 kj mol-1 330; carbon: electronegativity 2.55 Pauling scale 340; oxygen atoms have 8 electrons and the shell structure is 2.6 350; oxygen: electron affinity 141 kj mol-1 360; oxygen: electronegativity 3.44 Pauling scale 370; and XPS signals 380 of one embodiment.

Figure 4A:
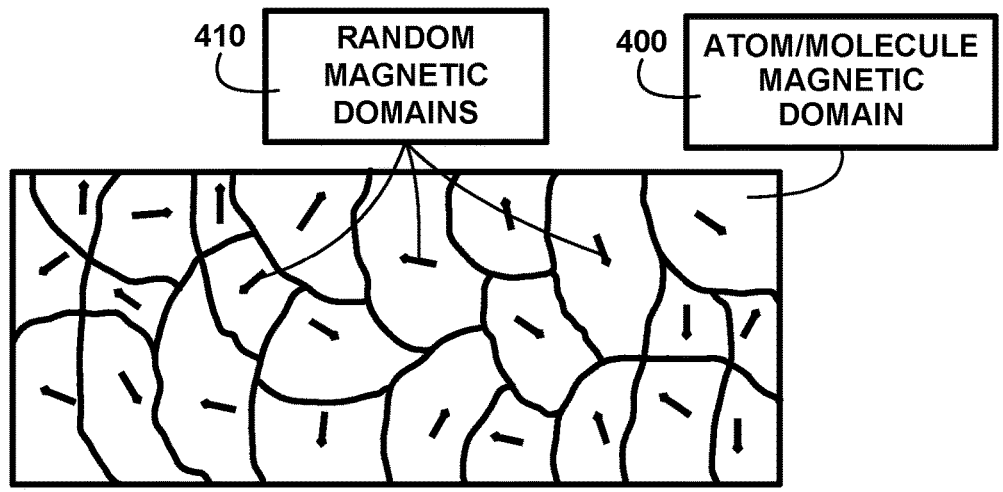
FIG. 4A shows for illustrative purposes only an example of random magnetic domains of one embodiment.

Random Magnetic Domains:

FIG. 4A shows for illustrative purposes only an example of random magnetic domains of one embodiment. FIG. 4A shows a plurality of atom/molecule magnetic domain 400 with random magnetic domains 410 of one embodiment.

Figure 4B:
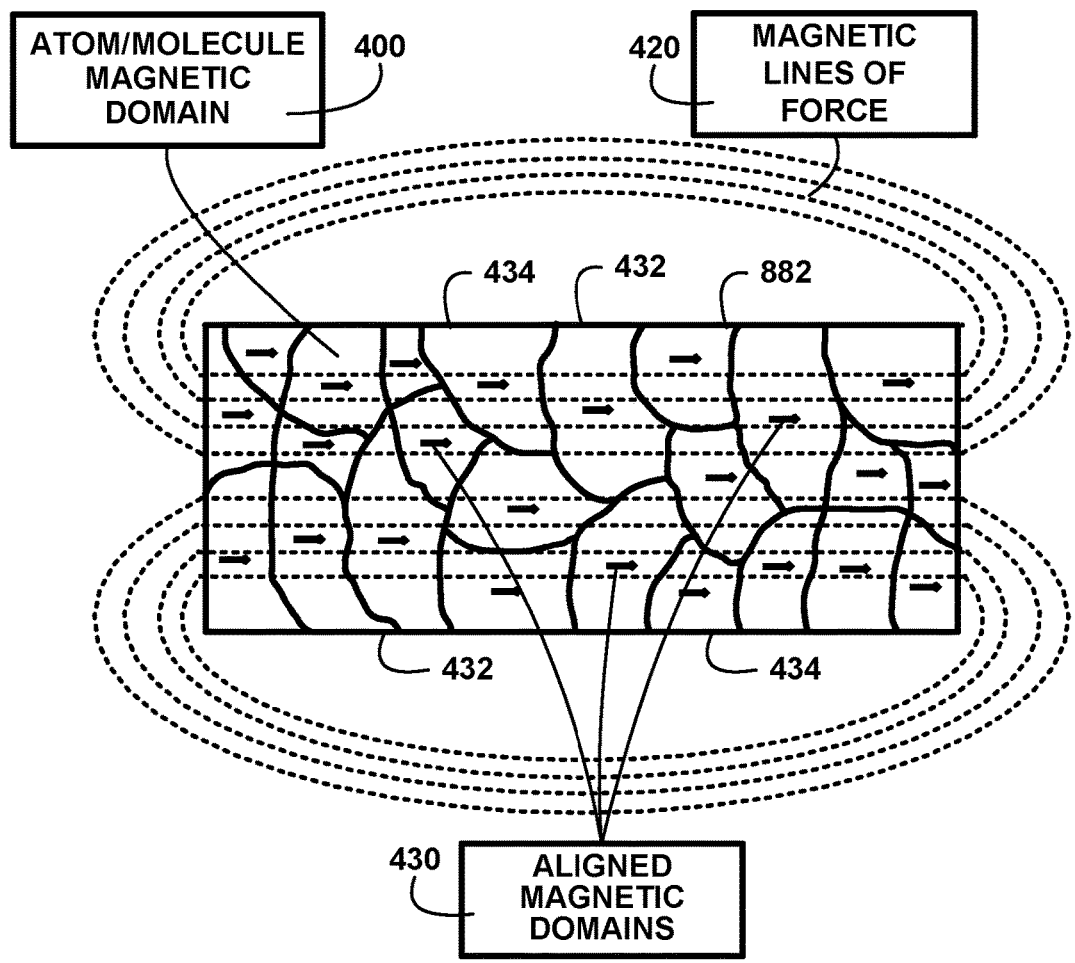
FIG. 4B shows for illustrative purposes only an example of aligned magnetic domains of one embodiment.

Aligned Magnetic Domains:

FIG. 4B shows for illustrative purposes only an example of aligned magnetic domains of one embodiment. FIG. 4B shows the same plurality of atom/molecule magnetic domain 400 with magnetic lines of force 420 applied. The magnetic lines of force 420 applied interact with the polarity of the molecule to reorient the molecule polarity into magnetic domains aligned 430 in the same direction. The atom/molecule magnetic domains are not shown being uniform to more easily illustrate the reorientation of the polarity in the same direction. In reality the atom/molecule magnetic domains form uniform shapes in line with the reoriented polarity direction of each molecule of one embodiment.

Figure 5A:
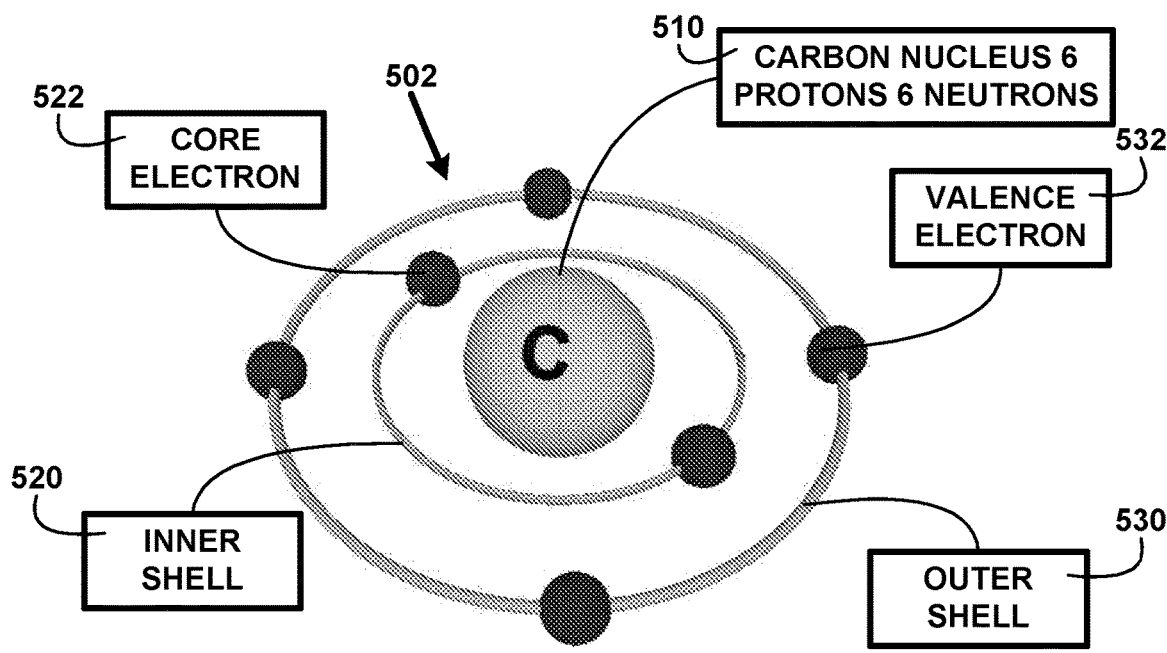
FIG. 5A shows for illustrative purposes only an example of carbon molecular structure of one embodiment.

Carbon Molecular Structure:

FIG. 5A shows for illustrative purposes only an example of carbon molecular structure of one embodiment. FIG. 5A shows a mineral carbon C 500 carbon molecule 502. The carbon nucleus 6 protons 6 neutrons 510 with an inner shell 520 with 2 core electrons 522 and an outer shell 530 with 4 valence electrons 532 of one embodiment.

Figure 5B:
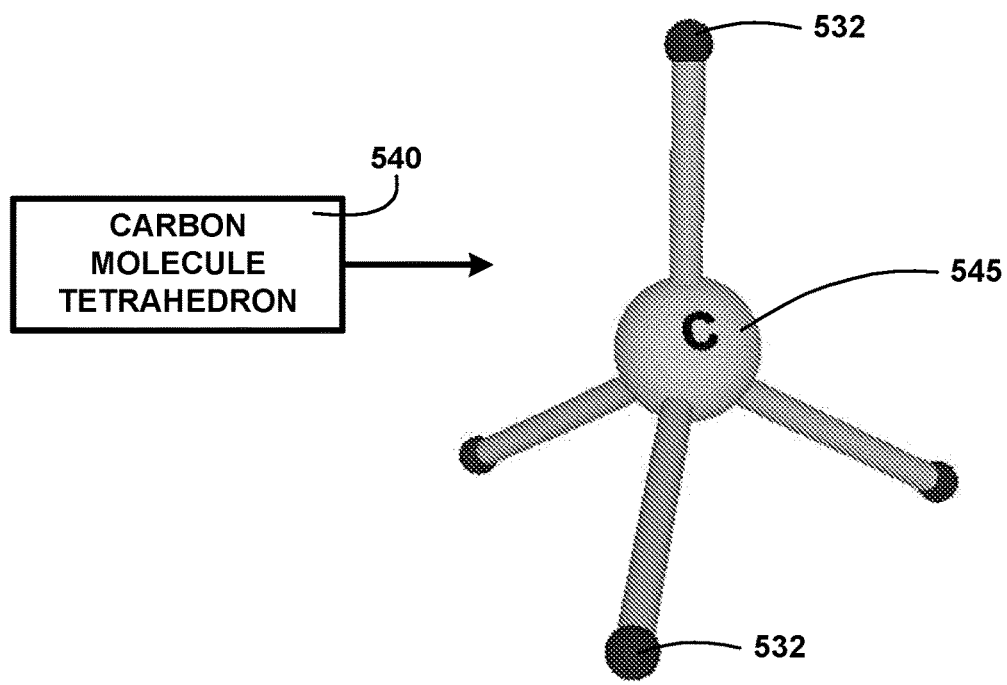
FIG. 5B shows for illustrative purposes only an example of carbon molecule tetrahedron of one embodiment.

Carbon Molecule Tetrahedron:

FIG. 5B shows for illustrative purposes only an example of carbon molecule tetrahedron of one embodiment. FIG. 5B shows a carbon molecule tetrahedron 540 structure with a carbon nucleus 545 and the 4 valence electrons 532 forming the tetrahedron configuration of one embodiment.

Figure 6:
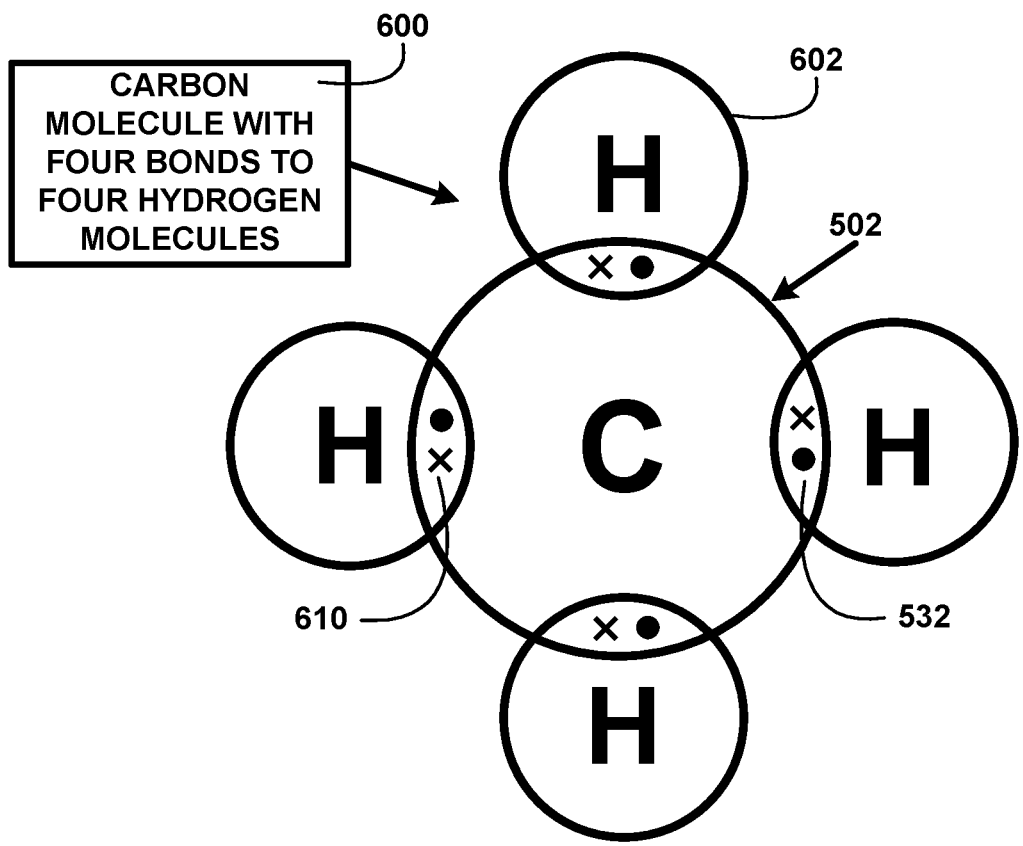
FIG. 6 shows for illustrative purposes only an example of carbon hydrogen bond of one embodiment.

Carbon Hydrogen Bond:

FIG. 6 shows for illustrative purposes only an example of carbon hydrogen bond of one embodiment. FIG. 6 shows for example a carbon molecule with four bonds to four hydrogen molecules 600. Each hydrogen valence electron 610 of each hydrogen molecule 602 bonds to one carbon valence electron 532 of the carbon molecule 502 of one embodiment.

Figure 7A:
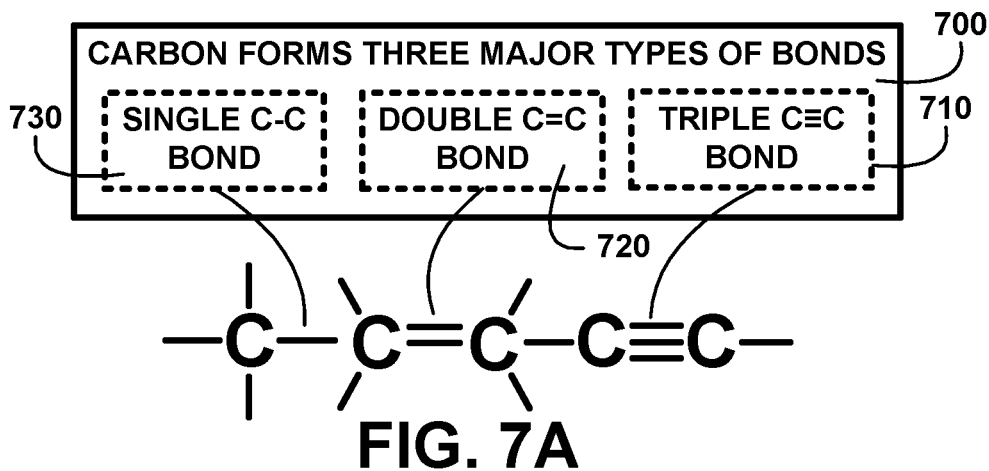
FIG. 7A shows for illustrative purposes only an example of carbon types of bonds of one embodiment.

Carbon Types of Bonds:

FIG. 7A shows for illustrative purposes only an example of carbon types of bonds of one embodiment. FIG. 7A shows carbon forms three major types of bonds 700 including a single C—C bond 730, a double C=C bond 720 and a triple C≡C bond 710 of one embodiment.

Figure 7B:
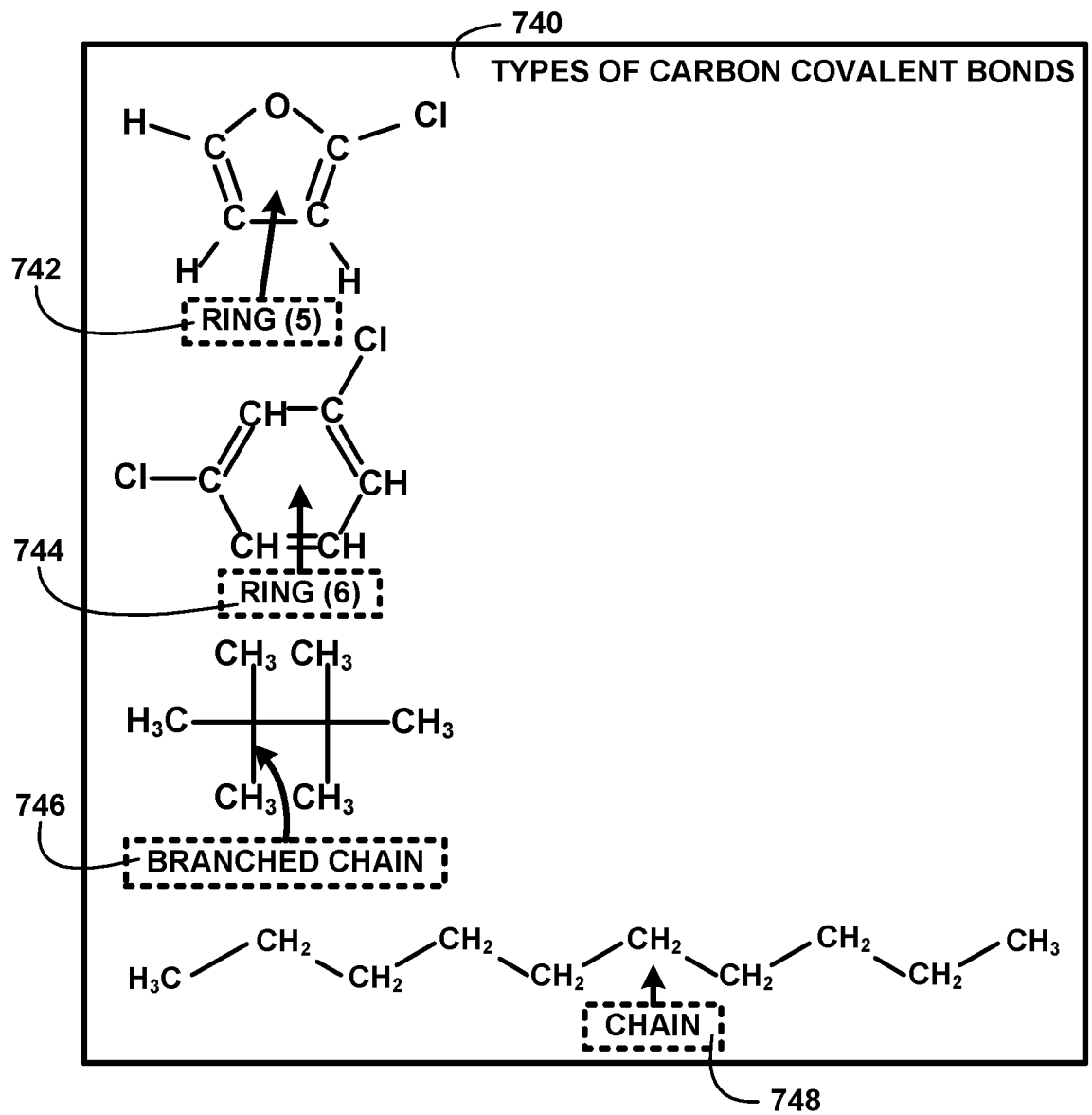
FIG. 7B shows for illustrative purposes only an example of carbon covalent bonds of one embodiment.

Carbon Covalent Bonds:

FIG. 7B shows for illustrative purposes only an example of carbon covalent bonds of one embodiment. FIG. 7B shows types of carbon covalent bonds 740 including a ring (5) 742 with 5 bonds, a ring (6) 744 with 6 bonds, a branched chain 746 and a chain 748 of one embodiment.

Figure 8:
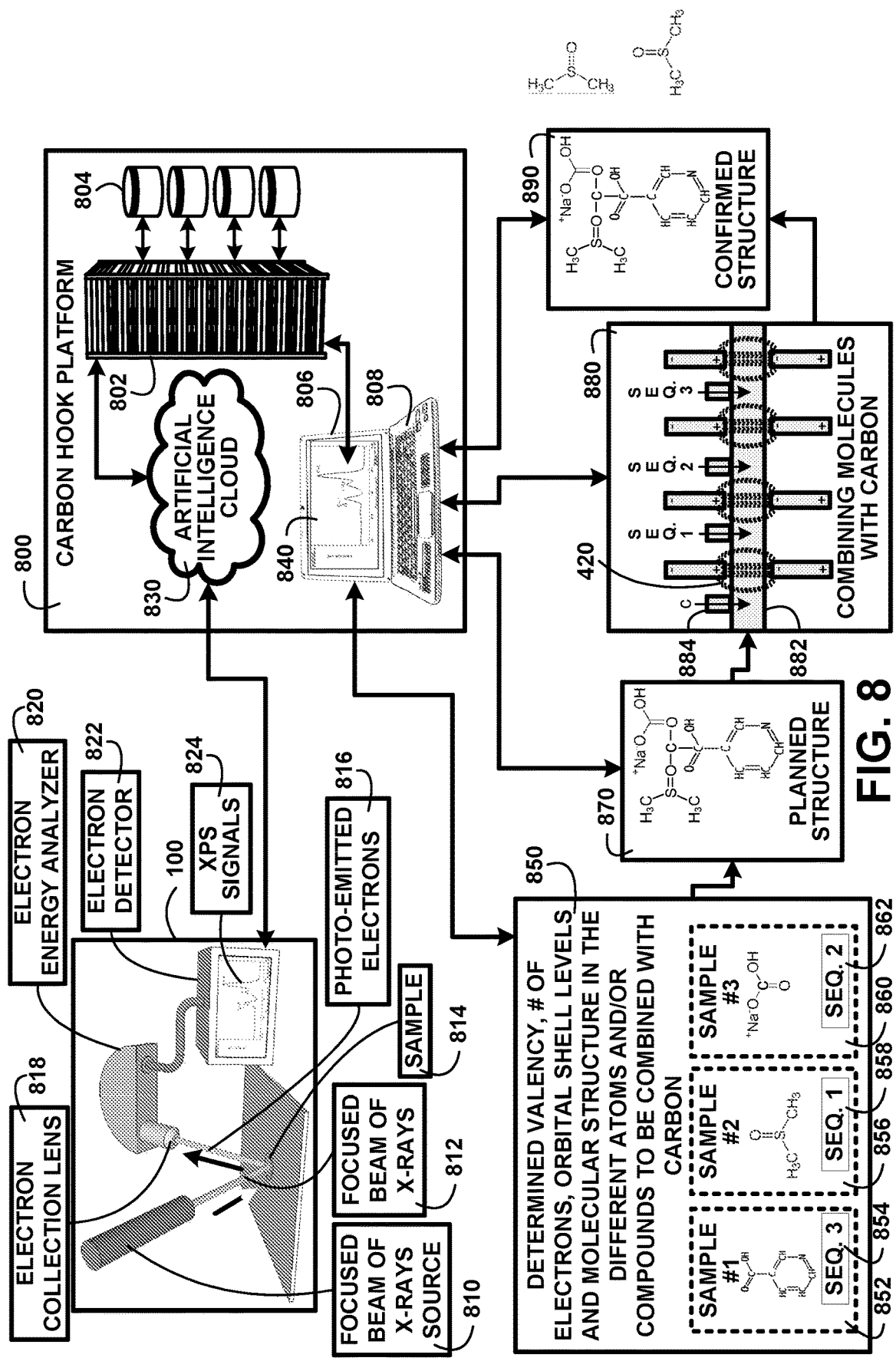
FIG. 8 shows for illustrative purposes only an example of carbon oriented compound apparatus of one embodiment.

Carbon Oriented Compound Apparatus:

FIG. 8 shows for illustrative purposes only an example of carbon oriented compound apparatus of one embodiment. FIG. 8 shows a carbon hook platform 800 including a network server 802, plurality of databases 804, network computer 808 and a carbon hook application 806. The process includes using an apparatus to determine the valency, number of electrons and orbital shell levels in the different atoms and/or compounds to be combined with carbon 100. This process includes a focused beam of x-rays source 810 producing a focused beam of x-rays 812 that are targeted to a compound sample 814.

Photo-emitted electrons 816 penetrate and "bounce" photo-emitted electrons 816 an electron collection lens 818. An electron energy analyzer 820 with an electron detector 822 analyzes the numbers and energy levels of the collected photo-emitted electrons 816 bounced off the compound sample 814 and convert the data into XPS signals 824. The analyzed data is transmitted to an artificial intelligence cloud 830 for compound sample 814 identified storage and determining the molecular structure the data signifies.

A display of XPS signals on the network computer 840 allows the operator to view the data in graphical form. The analysis results to create a determined valency, # of electrons, orbital shell levels and molecular structure in the different atoms and/or compounds to be combined with carbon 850. The different atoms and/or compounds to be combined with carbon include for example sample #1 852, sample #2 856 and sample #3 860. The electron energy analyzer 820 and artificial intelligence cloud 830 has determined a sequencing of the three samples which in this example includes sample #2 856 for seq. 1 858, sample #3 860 for seq. 2 862 and sample #1 852 for seq. 3 854 and a planned structure 870.

A sequential combination of carbon and other compounds 880 is performed using a sequence of magnetic lines of force 420 for seq. 1 858 carbon combination, seq. 2 862 carbon combination, and seq. 3 854 carbon combination. A process uses a sequential combination of carbon and other compounds magnetized chambers and inlets 882 wherein each sample is injected into the carbon suspended solution through an inlet while being exposed to magnetic lines of force 420 thereby aligning the sample molecules for a uniform bonding with the carbon molecules.

Upon completion a carbon and three samples combination resulting compound is reanalyzed for a confirmed structure 890 matching the planned structure 870. For each sample combination the magnitude and direction of the sequenced magnetic lines of force 420 can be set to a predetermined strength and orientation to affect the planned structural configuration of one embodiment.

Figures 9A, 9B:
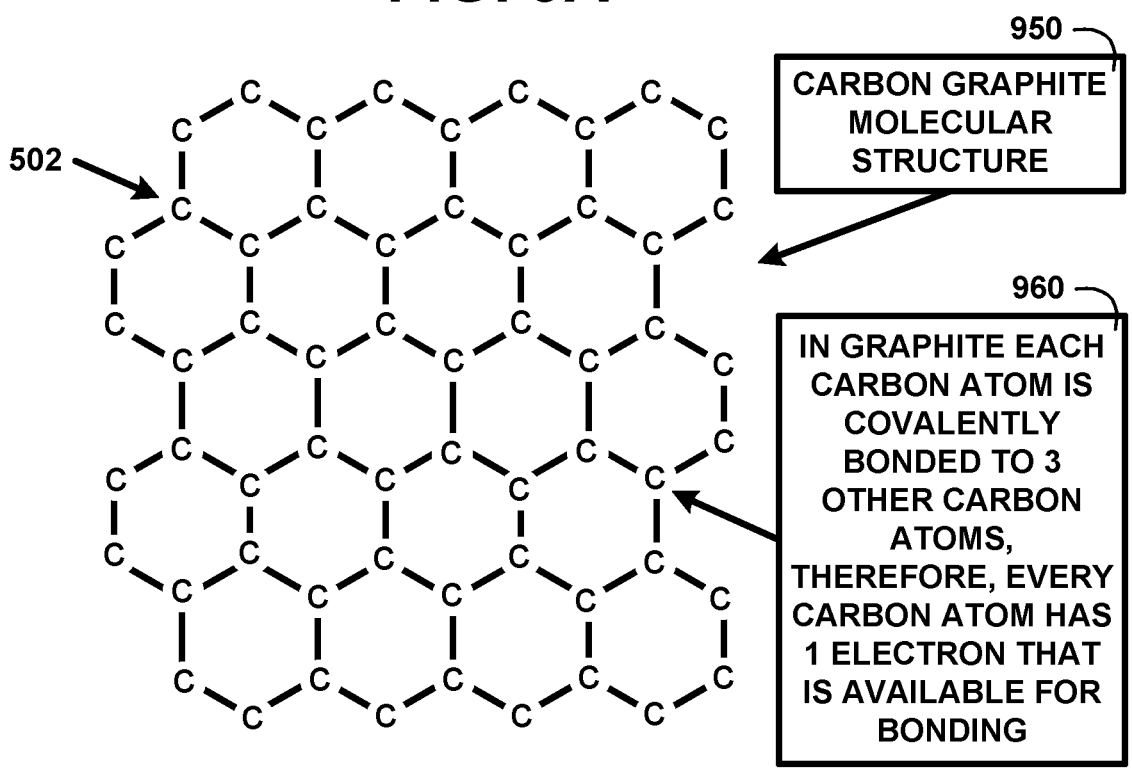
FIG. 9A shows a block diagram of an overview of activated carbon of one embodiment.
FIG. 9B shows for illustrative purposes only an example of graphite molecular structure of one embodiment.

Activated Carbon:

FIG. 9A shows a block diagram of an overview of activated carbon of one embodiment. FIG. 9A shows an example of activated carbon other common components 900 including a chemical formula 910 and corresponding concentration (ppm) 912. The common components include Al 920, 0.101 921; Ca 922, 0.2053 923; Ch2 924, 98.6 925; Cl 926, 0.0539 927; Cr 928, 0.0021 929; Cu 930, 0.0015 931; Fe 932, 0.2322 933; K 934, 0.4539 935; Mg 936, 0.0252 937; Mn 938, 0.0066 939; Mo 940, 0.001 941; Si 942, 0.0619 943 of one embodiment.

Graphite Molecular Structure:

FIG. 9B shows for illustrative purposes only an example of graphite molecular structure of one embodiment. FIG. 9B shows a plurality of the carbon molecule 502 in an example of a carbon graphite molecular structure 950. In graphite each carbon atom is covalently bonded to 3 other carbon atoms, therefore, every carbon atom has 1 electron that is available for bonding 960. The carbon graphite molecular structure 950 is also found in a 3 tier version of the molecular structure of one embodiment.

Essential Vitamins and Minerals:

Essential vitamins and minerals are required by the human body for cellular level functions. Vitamins are a group of substances that are needed for normal cell function, growth, and development. This means that these vitamins are required for the body to work properly. They include Vitamin A, Vitamin C, Vitamin D, Vitamin E, Vitamin K, Vitamin B1 (thiamine), Vitamin B2 (riboflavin), Vitamin B3 (niacin), Pantothenic acid (B5), Biotin (B7), Vitamin B6, Vitamin B12 (cyanocobalamin) and Folate (folic acid and B9). Some "vitamin-like factors" are also needed by the body including nutrient Choline and Carnitine.

A vitamin deficiency occurs when you do not get enough of a certain vitamin. Vitamin deficiency can cause health problems. Not eating enough fruits, vegetables, beans, lentils, whole grains and fortified dairy foods may increase your risk for health problems, including heart disease, cancer, and poor bone health (osteoporosis). Vitamin functions include:

Vitamin A helps form and maintains healthy teeth, bones, soft tissue, mucous membranes, and skin.

Vitamin B6 is also called pyridoxine.

Vitamin B6 helps form red blood cells and to maintain brain function. This vitamin also plays an important role in the proteins that are part of many chemical reactions in the body. The more protein you eat the more pyridoxine your body requires.

Vitamin B12, like the other B vitamins, is important for metabolism. It also helps form red blood cells and maintains the central nervous system.

Vitamin C, also called ascorbic acid, is an antioxidant that promotes healthy teeth and gums. It helps the body absorb iron and maintain healthy tissue. It is also essential for wound healing.

Vitamin D is also known as the "sunshine vitamin," since it is made by the body after being in the sun. Ten to 15 minutes of sunshine 3 times a week is enough to produce the body's requirement of vitamin D for most people at most latitudes. People who do not live in sunny places may not make enough vitamin D. It is very hard to get enough vitamin D from food sources alone. Vitamin D helps the body absorb calcium. You need calcium for the normal development and maintenance of healthy teeth and bones. It also helps maintain proper blood levels of calcium and phosphorus.

Vitamin E is an antioxidant also known as tocopherol. It helps the body form red blood cells and use vitamin K.

Vitamin K is needed because without it, blood would not stick together (coagulate). Some studies suggest that it is important for bone health.

Biotin is essential for the metabolism of proteins and carbohydrates, and in the production of hormones and cholesterol.

Niacin is a B vitamin that helps maintain healthy skin and nerves. It also has cholesterol-lowering effects at higher doses.

Folate works with vitamin B12 to help form red blood cells. It is needed for the production of DNA, which controls tissue growth and cell function. Any woman who is pregnant should be sure to get enough folate. Low levels of folate are linked to birth defects such as spina bifida. Many foods are now fortified with folic acid.

Pantothenic acid is essential for the metabolism of food. It also plays a role in the production of hormones and cholesterol.

Riboflavin (vitamin B2) works with the other B vitamins. It is important for body growth and the production of red blood cells.

Thiamine (vitamin B1) helps the body cells change carbohydrates into energy. Getting enough carbohydrates is very important during pregnancy and breastfeeding. It is also essential for heart function and healthy nerve cells.

Choline helps in normal functioning of the brain and nervous system. Lack of choline can cause swelling in liver.

Carnitine helps the body to change fatty acids into energy.

There are 12 minerals deemed essential for proper human nutrition. They are calcium, iron, phosphorus, iodine, magnesium, zinc, selenium, copper, manganese, chromium, molybdenum, and chlorine.

Essential minerals are those necessary for human health and are classified into two equally important groups: major minerals and trace minerals. The major minerals, which are used and stored in large quantities in the body, are calcium, chloride, magnesium, phosphorus, potassium, sodium, and sulfur. The trace minerals are just as vital to our health as the major minerals, but we don't need large amounts. Minerals in this category include chromium, copper, fluoride, iodine, iron, manganese, molybdenum, selenium, and zinc. The following describes the functions some of the essential minerals are necessary for human health.

Calcium builds bones and teeth; activates enzymes throughout the body; helps regulate blood pressure; and helps muscles to contract, nerves to send messages, and blood to clot.

Chromium helps maintain normal blood sugar levels and helps cells draw energy from blood sugar.

Copper assists with metabolizing fuel, making red blood cells, regulating neurotransmitters, and mopping up free radicals.

Iron helps make hemoglobin (the oxygen-carrying chemical in the body's red blood cells) and myoglobin (a protein in muscle cells). Iron is essential for activating certain enzymes and for making amino acids, collagen, neurotransmitters, and hormones.

Magnesium, like calcium, builds bones and teeth. It also helps to regulate blood pressure and blood sugar and enables muscles to contract, nerves to send messages, blood to clot, and enzymes to work.

Manganese helps form bones and helps metabolize amino acids, cholesterol, and carbohydrates.

Molybdenum activates several enzymes that break down toxins and prevents the buildup of harmful sulfites in the body.

Potassium balances fluids in the body, helps to maintain a steady heartbeat and to make muscles contract, and may benefit bones and blood pressure.

Sodium balances fluids in the body, helps send nerve impulses, and helps make muscles contract.

Zinc helps blood clot, helps make proteins and DNA, bolsters the immune system, and helps with wound healing and cell division of one embodiment.

Figure 10A:
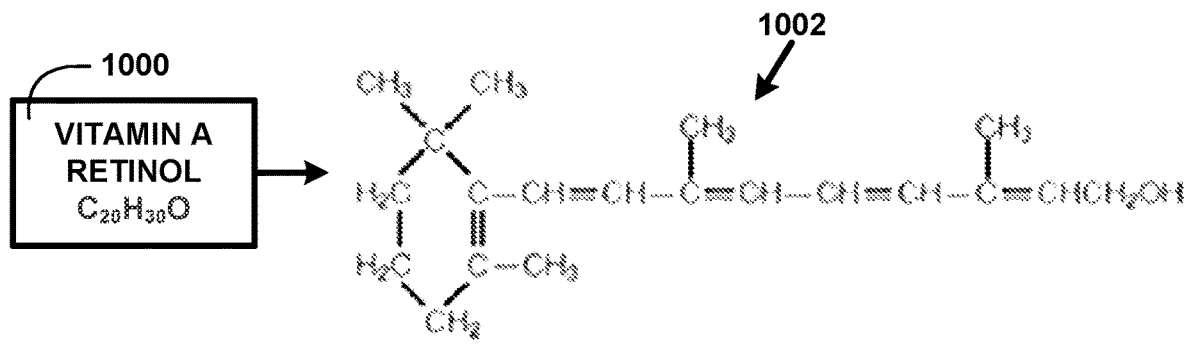
FIG. 10A shows for illustrative purposes only an example of vitamin a of one embodiment.

Vitamin A:

FIG. 10A shows for illustrative purposes only an example of vitamin a of one embodiment. FIG. 10A shows the chemical formula for vitamin A retinol $C_{20}H_{30}O$ 1000 and the vitamin A molecular structure 1002 of one embodiment.

Figure 10B:
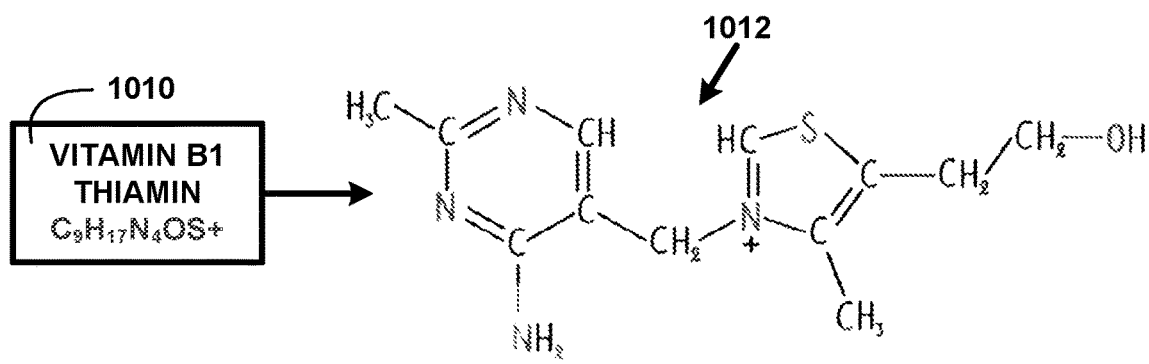
FIG. 10B shows for illustrative purposes only an example of vitamin b1 of one embodiment.

Vitamin B1:

FIG. 10B shows for illustrative purposes only an example of vitamin b1 of one embodiment. FIG. 10B shows the chemical formula for vitamin B1 thiamin $C_9H_{17}N_4OS+$ 1010 and a vitamin B1 molecular structure 1012 of one embodiment.

Figure 10C:
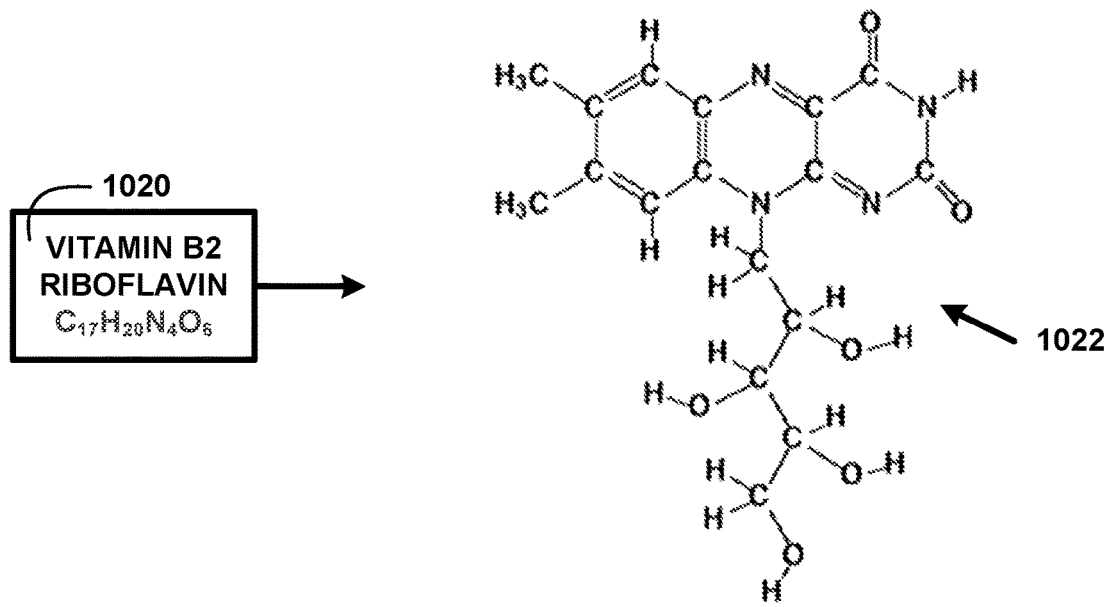
FIG. 10C shows for illustrative purposes only an example of vitamin b2 of one embodiment.

Vitamin B2:

FIG. 10C shows for illustrative purposes only an example of vitamin B2 of one embodiment. FIG. 10C shows the chemical formula for vitamin B2 riboflavin $C_{17}H_{20}N_4O_6$ 1020 and a vitamin B2 molecular structure 1022 of one embodiment.

Figure 11A:
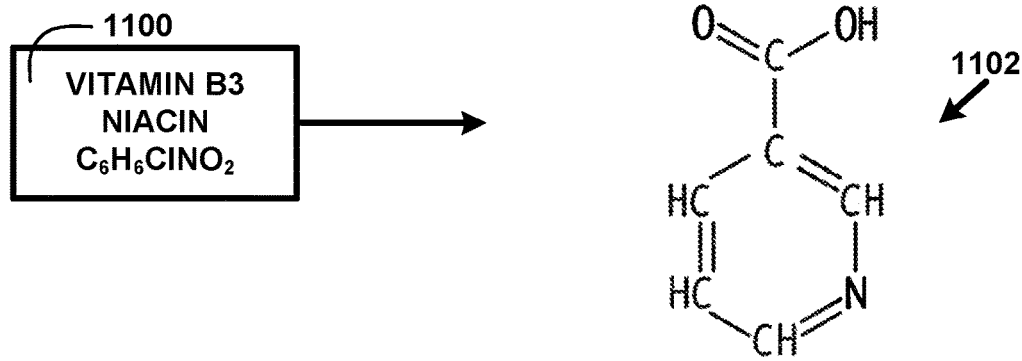
FIG. 11A shows for illustrative purposes only an example of vitamin b3 of one embodiment.

Vitamin B3:

FIG. 11A shows for illustrative purposes only an example of vitamin B3 of one embodiment. FIG. 11A shows the chemical formula for vitamin B3 niacin c6h6clno2 1100 and a vitamin B3 molecular structure 1102 of one embodiment.

Figure 11B:
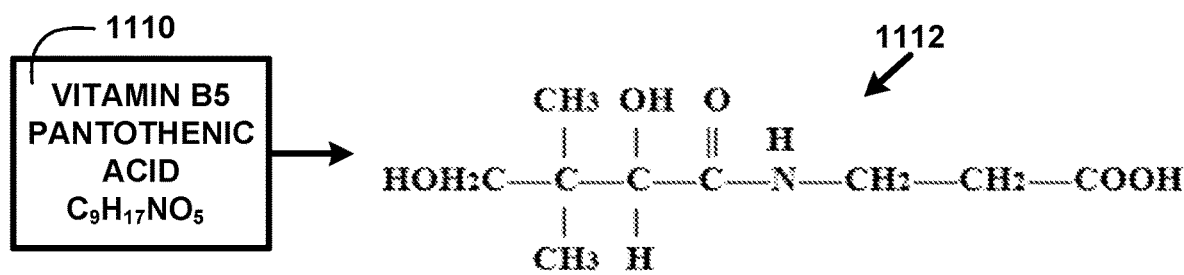
FIG. 11B shows for illustrative purposes only an example of vitamin b5 of one embodiment.

Vitamin B5:

FIG. 11B shows for illustrative purposes only an example of vitamin B5 of one embodiment. FIG. 11B shows the chemical formula for vitamin B5 pantothenic acid $C_9H_{17}NO_5$ 1110 and a vitamin B5 molecular structure 1112 of one embodiment.

Figure 11C:
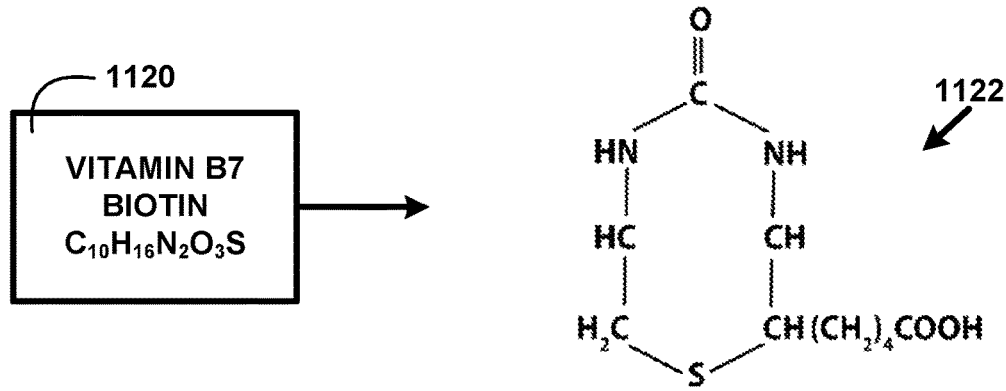
FIG. 11C shows for illustrative purposes only an example of vitamin b7 of one embodiment.

Vitamin B7:

FIG. 11C shows for illustrative purposes only an example of vitamin B7 of one embodiment. FIG. 11C shows the chemical formula for vitamin B7 biotin $C_{10}H_{16}N_2O_3S$ 1120 and a vitamin B7 molecular structure 1122 of one embodiment.

Figure 11D:
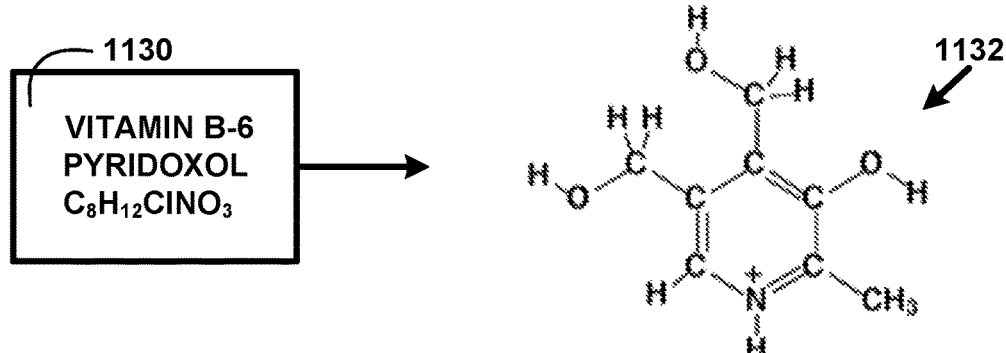
FIG. 11D shows for illustrative purposes only an example of vitamin b-6 of one embodiment.

Vitamin B-6:

FIG. 11D shows for illustrative purposes only an example of vitamin B-6 of one embodiment. FIG. 11D shows the chemical formula for vitamin B-6 pyridoxol $C_8H_{12}CLNO_3$ 1130 and a vitamin B-6 molecular structure 1132 of one embodiment.

Figure 12A:
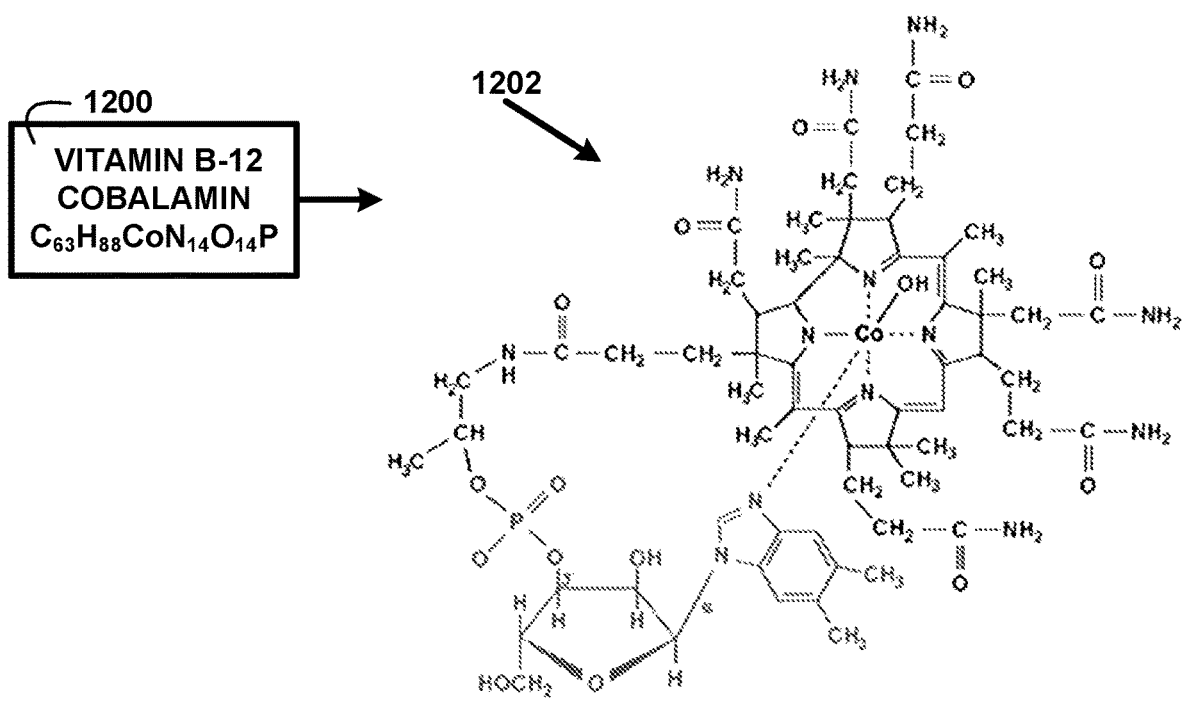
FIG. 12A shows for illustrative purposes only an example of vitamin b-12 of one embodiment.

Vitamin B-12:

FIG. 12A shows for illustrative purposes only an example of vitamin B-12 of one embodiment. FIG. 12A shows the chemical formula for vitamin B-12 cobalamin $C_{63}H_{88}CON_{14}O_{14}P$ 1200 and a vitamin B-12 molecular structure 1202 of one embodiment.

Figure 12B:
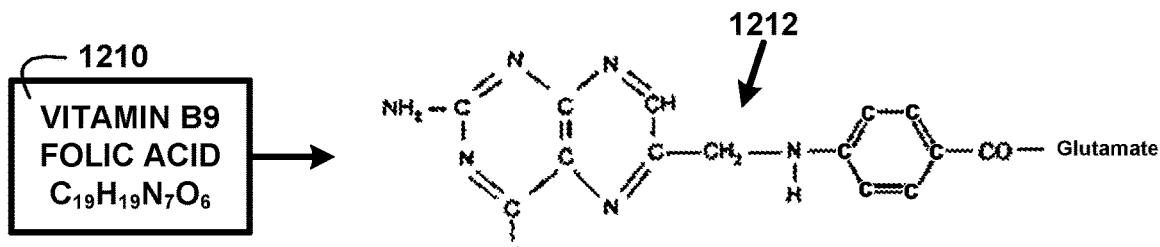
FIG. 12B shows for illustrative purposes only an example of vitamin b9 of one embodiment.

Vitamin B9:

FIG. 12B shows for illustrative purposes only an example of vitamin B9 of one embodiment. FIG. 12B shows the chemical formula for vitamin B9 folic acid $C_{19}H_{19}N_7O_6$ 1210 and a vitamin B9 molecular structure 1212 of one embodiment.

Figure 12C:
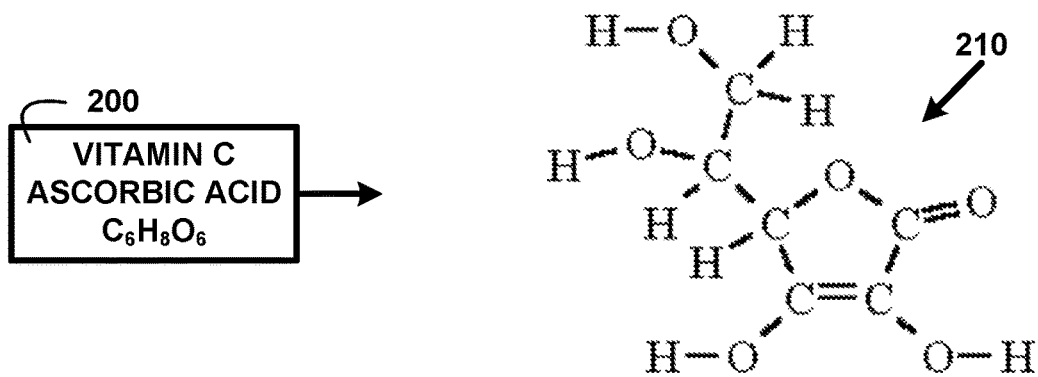
FIG. 12C shows for illustrative purposes only an example of vitamin c of one embodiment.

Vitamin C:

FIG. 12C shows for illustrative purposes only an example of vitamin C of one embodiment. FIG. 12C shows the chemical formula for vitamin C ascorbic acid $C_6H_8O_6$ 200 and a vitamin C molecular structure 210 of one embodiment.

Figure 13A:
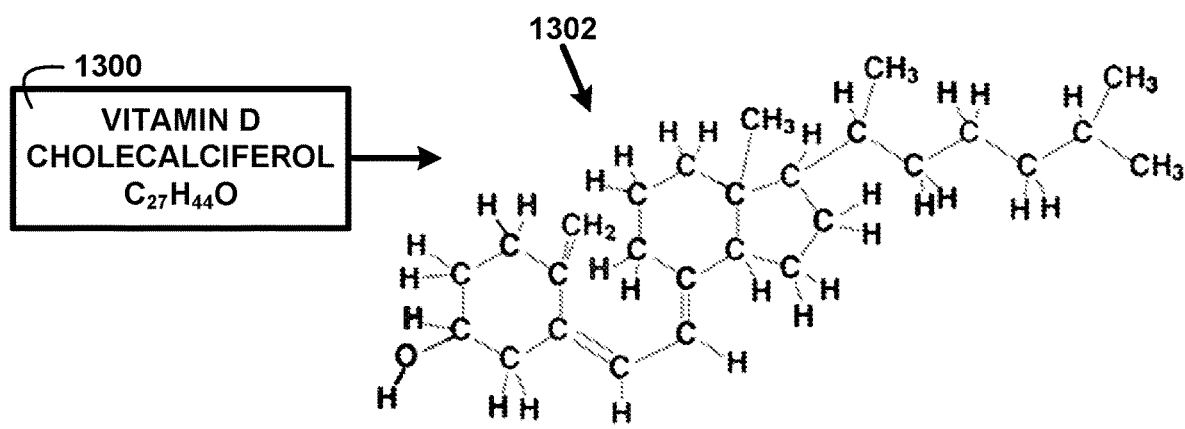
FIG. 13A shows for illustrative purposes only an example of vitamin d of one embodiment.

Vitamin D:

FIG. 13A shows for illustrative purposes only an example of vitamin D of one embodiment. FIG. 13A shows the chemical formula for vitamin D cholecalciferol $C_{27}H_{44}O$ 1300 and a vitamin D molecular structure 1302 of one embodiment.

Figure 13B:
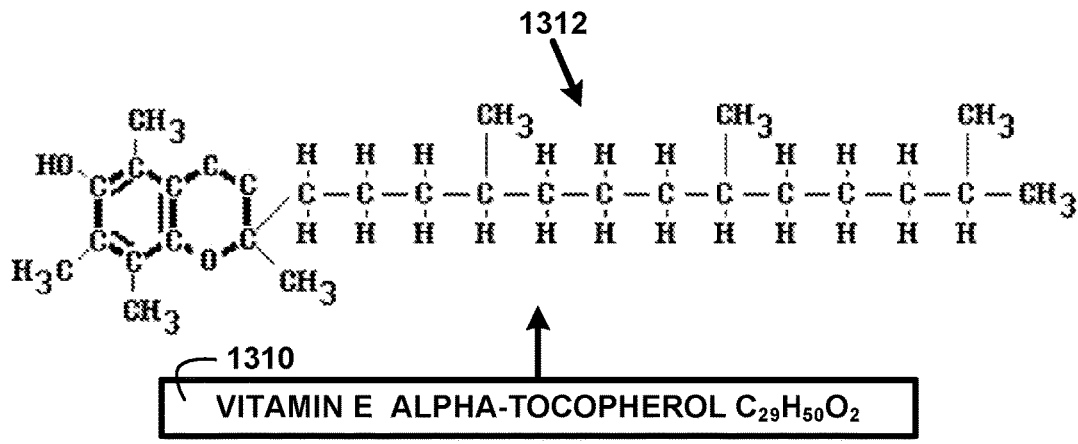
FIG. 13B shows for illustrative purposes only an example of vitamin e of one embodiment.

Vitamin E:

FIG. 13B shows for illustrative purposes only an example of vitamin E of one embodiment. FIG. 13B shows the chemical formula for vitamin E alpha-tocopherol $C_{29}H_{50}O_2$ 1310 and a vitamin E molecular structure 1312 of one embodiment.

Figure 13C:
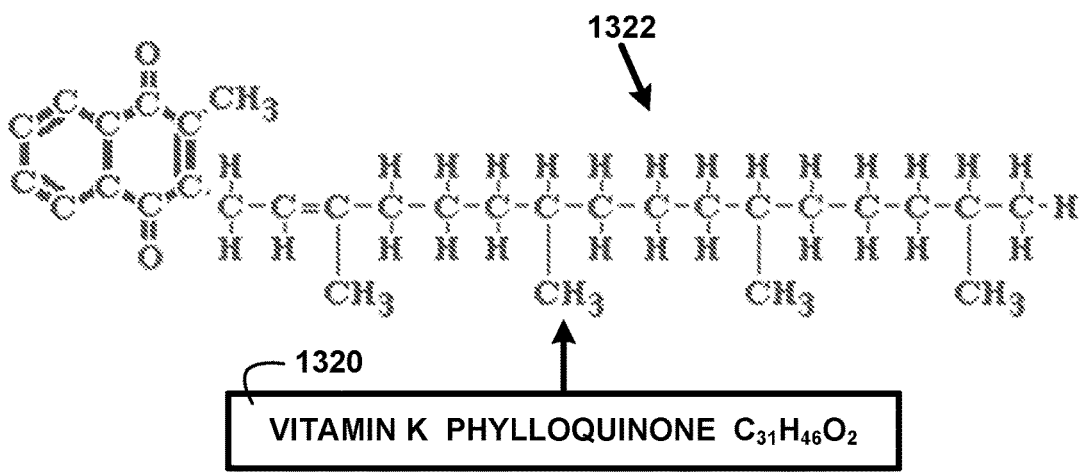
FIG. 13C shows for illustrative purposes only an example of vitamin k of one embodiment.

Vitamin K:

FIG. 13C shows for illustrative purposes only an example of vitamin K of one embodiment. FIG. 13C shows the chemical formula for vitamin K phylloquinone $C_{31}H_{46}O_2$ 1320 and a vitamin K molecular structure 1322 of one embodiment.

The minerals shown are compounds of the minerals as approved for human consumption by the NIH.

Figure 14A:
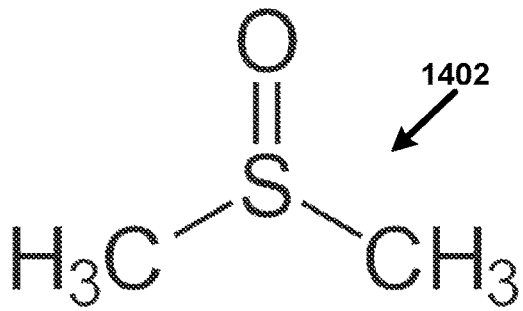
FIG. 14A shows for illustrative purposes only an example of mineral sulfur of one embodiment.

Mineral Sulfur:

FIG. 14A shows for illustrative purposes only an example of mineral sulfur of one embodiment. FIG. 14A shows the chemical formula for mineral sulfur dimethyl sulfoxide $(CH_3)2SO$ 1400 and a mineral dimethyl sulfoxide molecular structure 1402 of one embodiment.

Figure 14B:
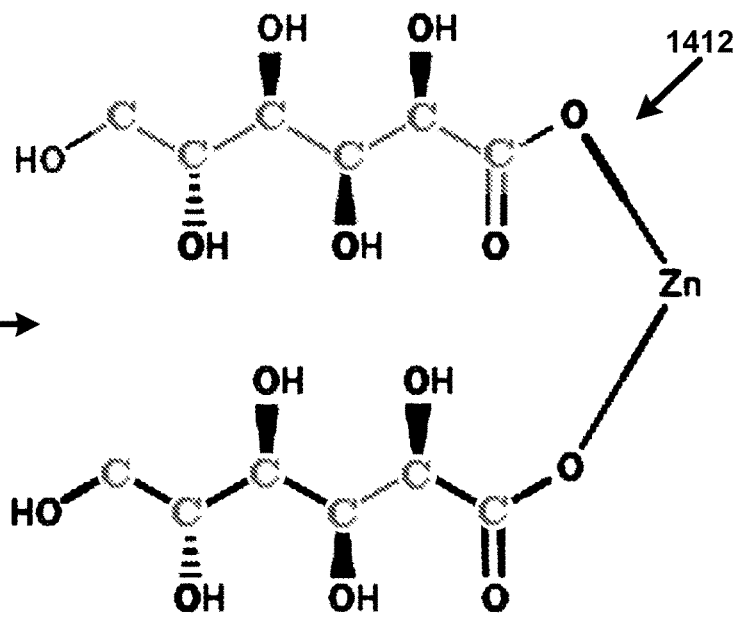
FIG. 14B shows for illustrative purposes only an example of mineral zinc of one embodiment.

Mineral Zinc:

FIG. 14B shows for illustrative purposes only an example of mineral zinc of one embodiment. FIG. 14B shows the chemical formula for mineral zinc gluconate $C_{12}H_{22}O_{14}Zn$ 1410 and a mineral zinc gluconate structure 1412 of one embodiment.

Figure 14C:
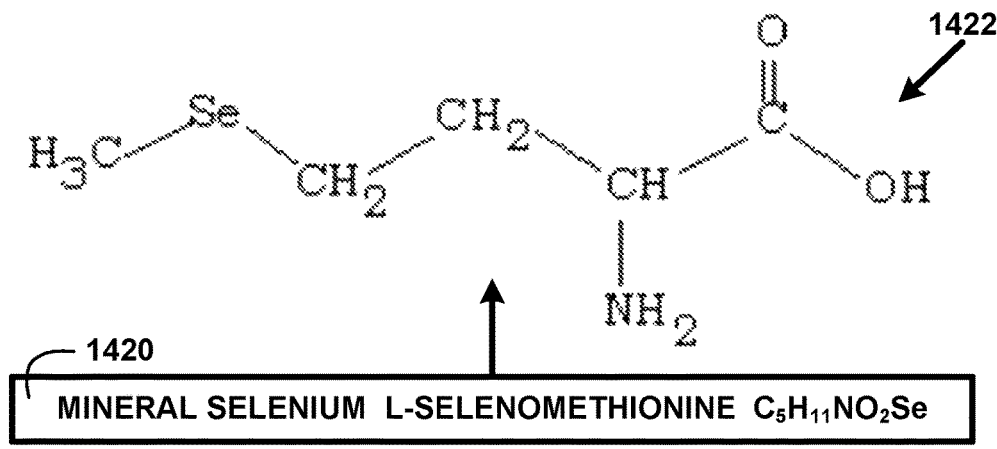
FIG. 14C shows for illustrative purposes only an example of mineral selenium of one embodiment.

Mineral Selenium:

FIG. 14C shows for illustrative purposes only an example of mineral selenium of one embodiment. FIG. 14C shows the chemical formula for mineral selenium l-selenomethionine $C_5H_{11}NO_2Se$ 1420 and a mineral l-selenomethionine molecular structure 1422 of one embodiment.

Figure 15A:
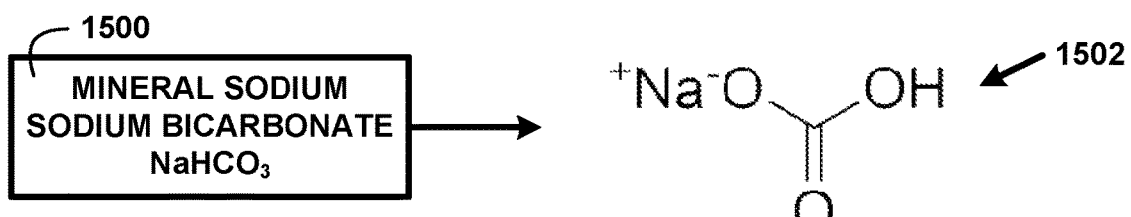
FIG. 15A shows for illustrative purposes only an example of mineral sodium of one embodiment.

Mineral Sodium:

FIG. 15A shows for illustrative purposes only an example of mineral sodium of one embodiment. FIG. 15A shows the chemical formula for mineral sodium bicarbonate $NaHCO_3$ 1500 and a mineral sodium bicarbonate molecular structure 1502 of one embodiment.

Figure 15B:
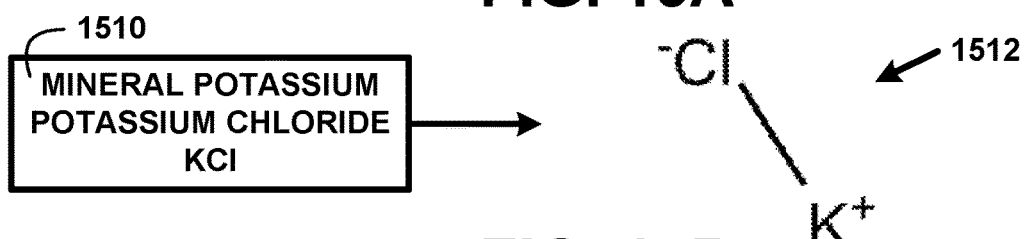
FIG. 15B shows for illustrative purposes only an example of mineral potassium of one embodiment.

Mineral Potassium:

FIG. 15B shows for illustrative purposes only an example of mineral potassium of one embodiment. FIG. 15B shows the chemical formula for mineral potassium chloride $KCl$ 1510 and a mineral potassium chloride molecular structure 1512 of one embodiment.

Figure 15C:
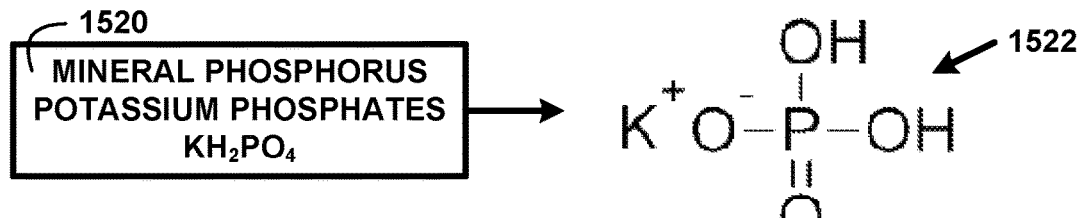
FIG. 15C shows for illustrative purposes only an example of mineral phosphorus of one embodiment.

Mineral Phosphorus:

FIG. 15C shows for illustrative purposes only an example of mineral phosphorus of one embodiment. FIG. 15C shows the chemical formula for mineral phosphorus potassium phosphates $KH_2PO_4$ 1520 and a mineral potassium phosphates molecular structure 1522 of one embodiment.

Figure 15D:
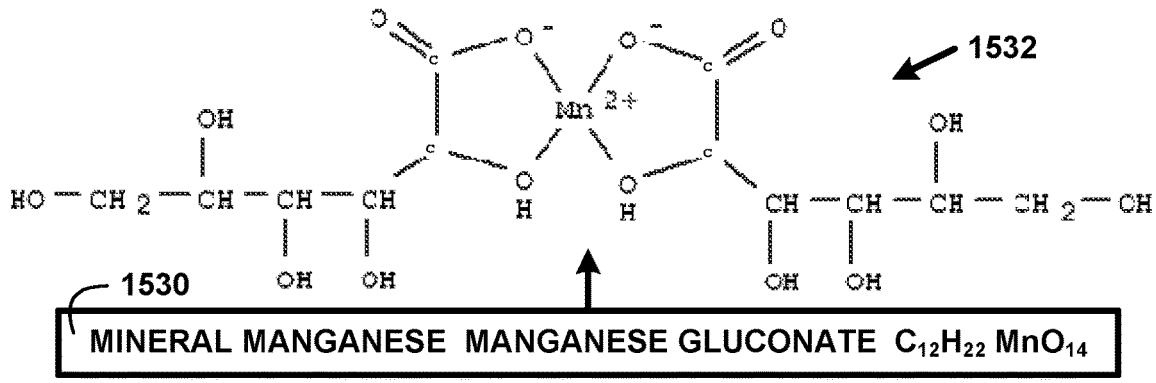
FIG. 15D shows for illustrative purposes only an example of mineral manganese of one embodiment.

Mineral Manganese:

FIG. 15D shows for illustrative purposes only an example of mineral manganese of one embodiment. FIG. 15D shows the chemical formula for mineral manganese gluconate $C_{12}H_{22}MnO_{14}$ 1530 and a mineral manganese gluconate molecular structure 1532 of one embodiment.

Figure 15E:
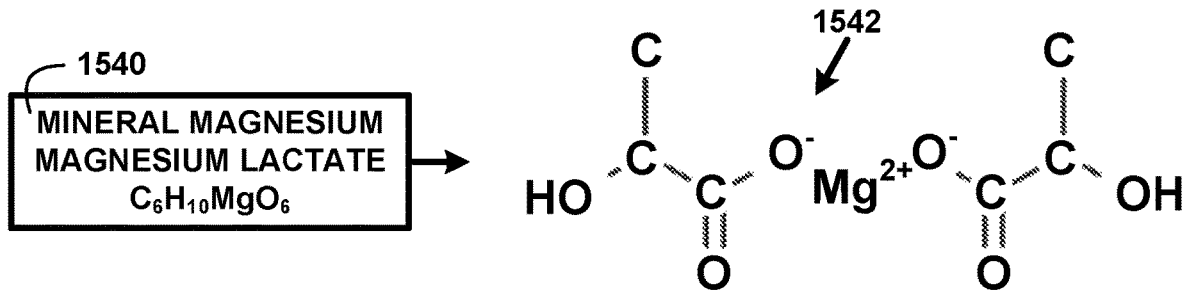
FIG. 15E shows for illustrative purposes only an example of mineral magnesium of one embodiment.

Mineral Magnesium:

FIG. 15E shows for illustrative purposes only an example of mineral magnesium of one embodiment. FIG. 15E shows the chemical formula for mineral magnesium lactate $C_6H_{10}MgO_6$ 1540 and a mineral magnesium lactate molecular structure 1542 of one embodiment.

Figure 16A:
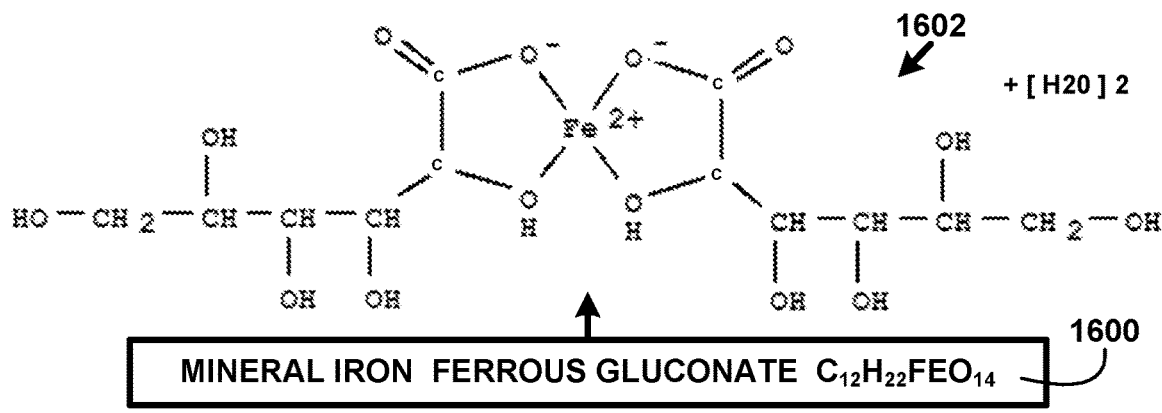
FIG. 16A shows for illustrative purposes only an example of mineral iron of one embodiment.

Mineral Iron:

FIG. 16A shows for illustrative purposes only an example of mineral iron of one embodiment. FIG. 16A shows the chemical formula for mineral iron ferrous gluconate $C_{12}H_{22}FeO_{14}$ 1600 and a mineral ferrous gluconate molecular structure 1602 of one embodiment.

Figure 16B:
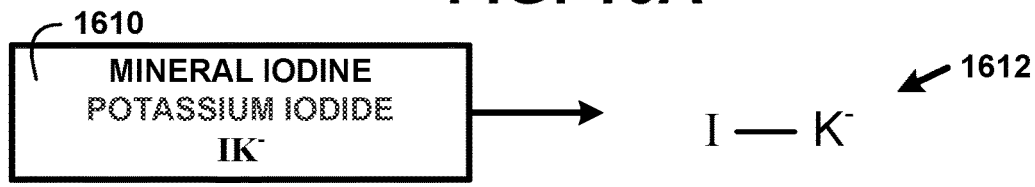
FIG. 16B shows for illustrative purposes only an example of mineral iodine of one embodiment.

Mineral Iodine:

FIG. 16B shows for illustrative purposes only an example of mineral iodine of one embodiment. FIG. 16B shows the chemical formula for mineral iodine potassium iodide $IK^-$ 1610 and a mineral potassium iodide molecular structure 1612 of one embodiment.

Figure 16C:
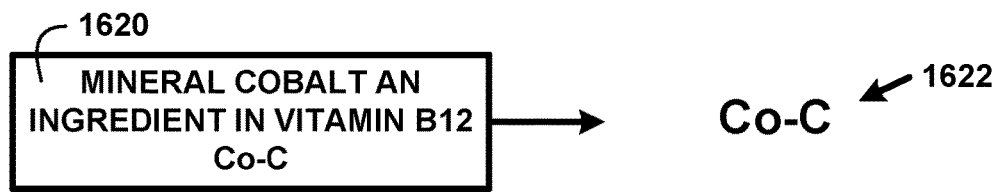
FIG. 16C shows for illustrative purposes only an example of mineral cobalt of one embodiment.

Mineral Cobalt:

FIG. 16C shows for illustrative purposes only an example of mineral cobalt of one embodiment. FIG. 16C shows the chemical formula for mineral cobalt an ingredient in vitamin $B_{12}$ $Co^-C$ 1620 and a mineral cobalt molecular structure 1622 of one embodiment.

Figure 16D:
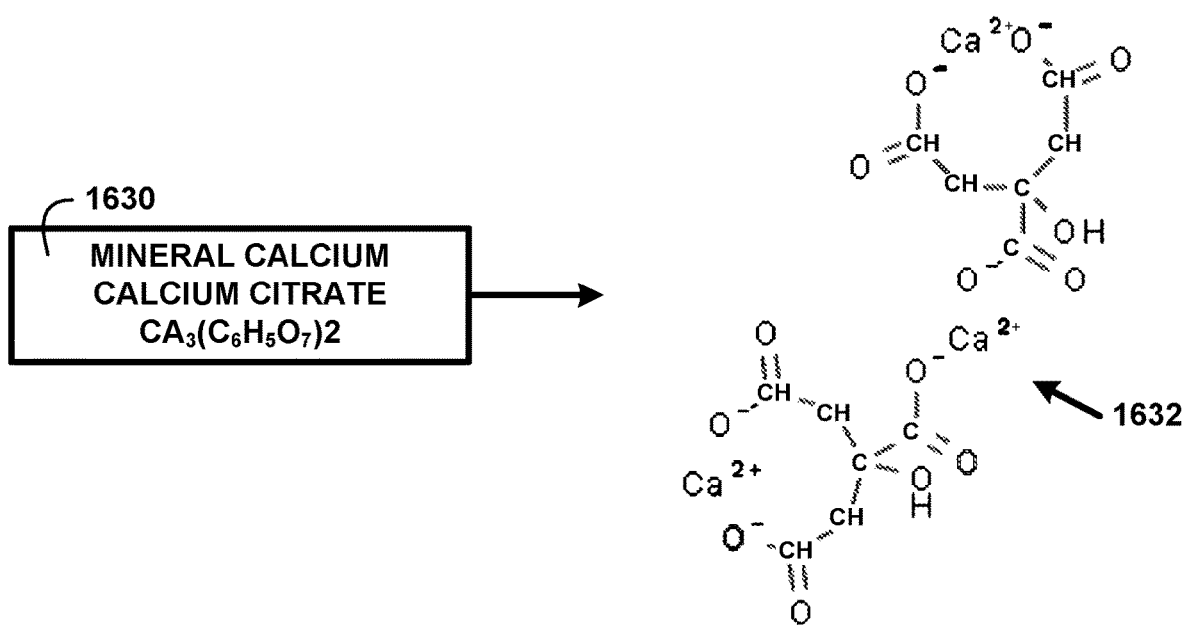
FIG. 16D shows for illustrative purposes only an example of mineral calcium of one embodiment.

Mineral Calcium:

FIG. 16D shows for illustrative purposes only an example of mineral calcium of one embodiment. FIG. 16D shows the chemical formula for mineral calcium citrate $Ca_3(C_6H_5O_7)2$ 1630 and a mineral calcium citrate molecular structure 1632 of one embodiment.

Figure 17A:
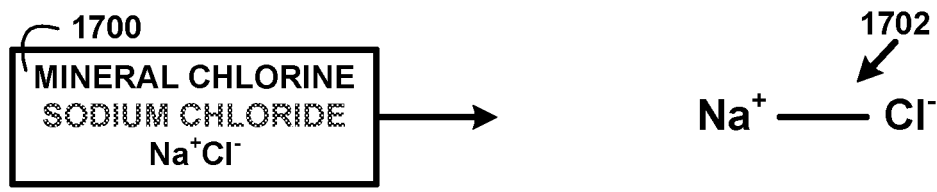
FIG. 17A shows for illustrative purposes only an example of mineral chlorine of one embodiment.

Mineral Chlorine:

FIG. 17A shows for illustrative purposes only an example of mineral chlorine of one embodiment. FIG. 17A shows the chemical formula for mineral chlorine sodium chloride $Na^+Cl^-$ 1700 and a mineral sodium chloride molecular structure 1702 of one embodiment.

Figure 17B:
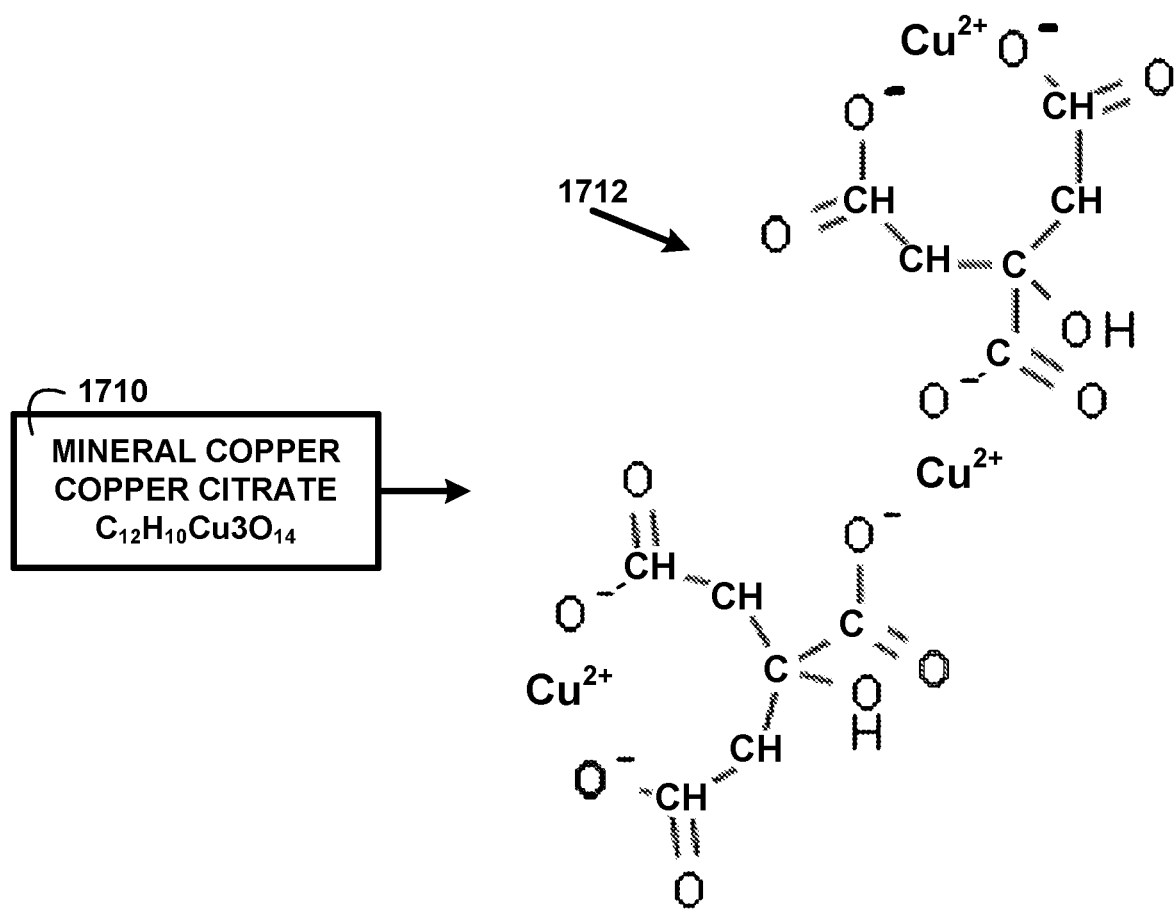
FIG. 17B shows for illustrative purposes only an example of mineral copper of one embodiment.

Mineral Copper:

FIG. 17B shows for illustrative purposes only an example of mineral copper of one embodiment. FIG. 17B shows the chemical formula for mineral copper citrate $C_{12}H_{10}Cu_3O_{14}$ 1710 and a mineral copper citrate molecular structure 1712 of one embodiment.

Figure 17C:
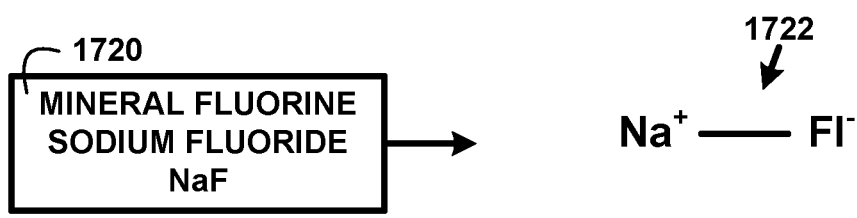
FIG. 17C shows for illustrative purposes only an example of mineral fluorine of one embodiment.

Mineral Fluorine:

FIG. 17C shows for illustrative purposes only an example of mineral fluorine of one embodiment. FIG. 17C shows the chemical formula for mineral fluorine sodium fluoride $NaF$ 1720 and a mineral sodium fluoride molecular structure 1722 of one embodiment.

Figure 18:
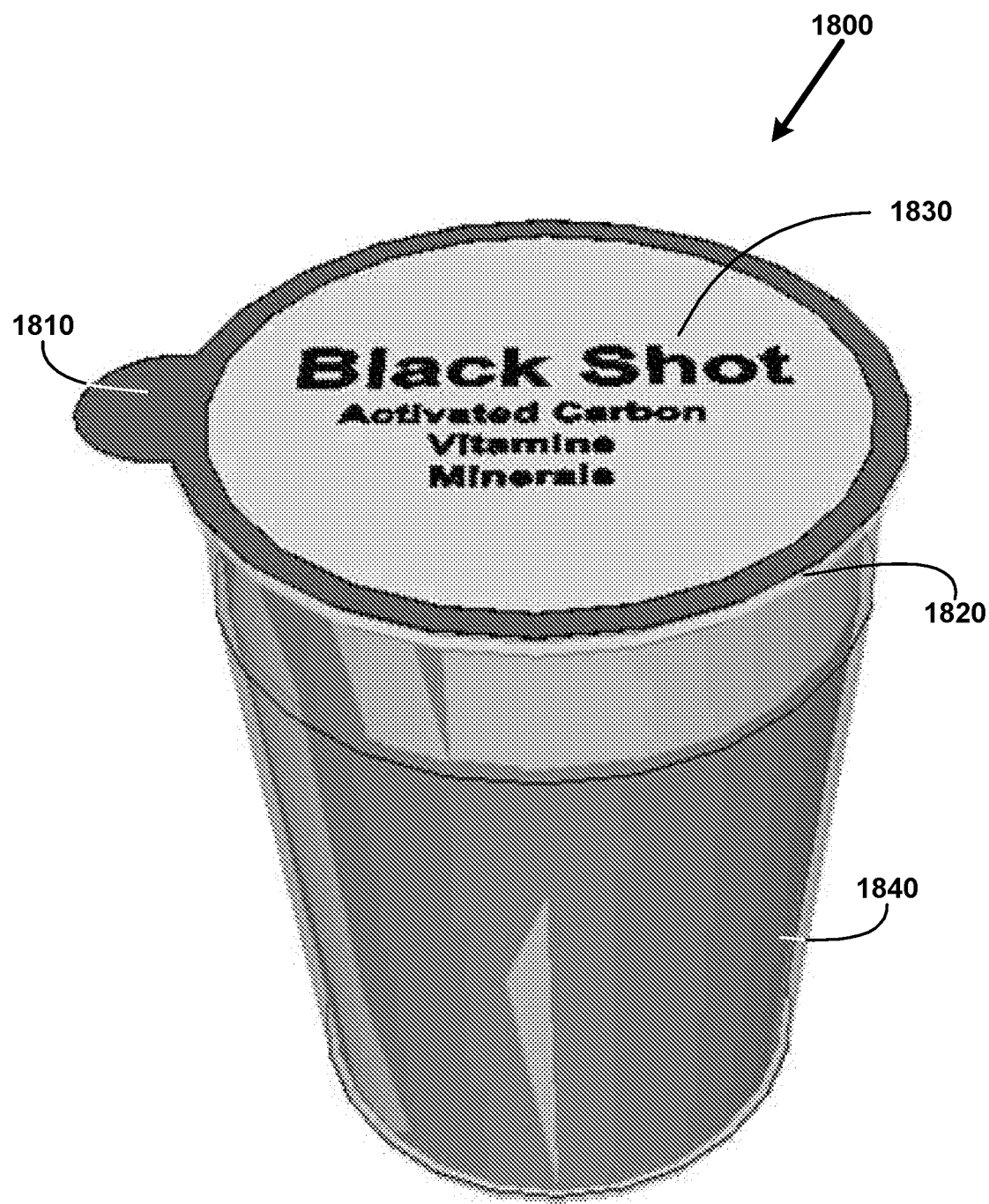
FIG. 18 shows for illustrative purposes only an example of black shot drink of one embodiment.

Black Shot Drink:

FIG. 18 shows for illustrative purposes only an example of black shot drink of one embodiment. FIG. 18 shows the formulation for a black shot drink 1800 containing activated carbon vitamins minerals 1830. The black shot drink 1800 is shown in a plastic cup 1820 with a flexible cover with pull tab 1810. An apparatus is used for forming and containerizing a beverage using the magnetically aligned final carbon combined compound with the carbon molecules including molecules of vitamins, mineral compounds, vitamin-like nutrients and factors and fulvic acid. The plastic cup 1820 contains the black carbon based beverage 1840 where the black color is derived from the suspended carbon ingredients of one embodiment.

Figure 19:
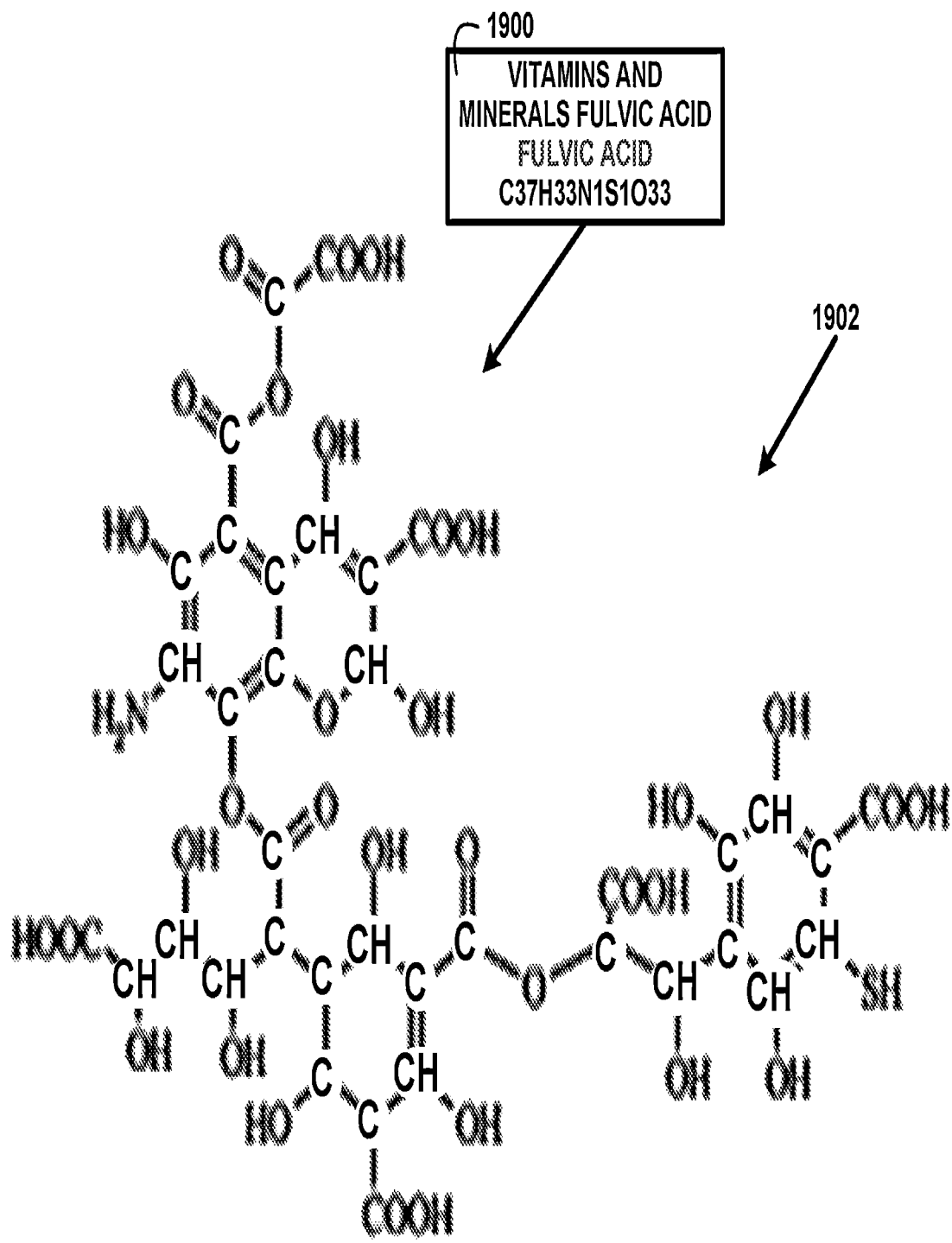
FIG. 19 shows for illustrative purposes only an example of fulvic acid vitamins and minerals of one embodiment.

Fulvic Acid Vitamins and Minerals:

FIG. 19 shows for illustrative purposes only an example of fulvic acid vitamins and minerals of one embodiment. FIG. 19 shows a fulvic acid molecular structure 1902 of the vitamins and minerals fulvic acid fulvic acid c37h33n1s1o33 1900 molecule. Fulvic acid is well known for its health benefits due to the unique properties and abundance of the essential vitamins and minerals required by the human body for cellular level functions. It is abundantly clear that the fulvic acid molecule is replete with carbon molecules. Fulvic acid also includes amounts of the nutrition a person needs on a daily basis including many vitamins and minerals including the trace minerals of one embodiment.

During decomposition, organic matter releases millions of beneficial microbes and chemically active compounds containing a variety of beneficial nutrients. Fulvic acid is among the potent compounds released in the decomposition process. Among other nutritional benefits, fulvic acid contains an assortment of fatty acids, hormones, vitamins, minerals, ketones, and flavonoids, nutrients needed for healthy cell and body development.

Fulvic acid contributes to improved digestive health, better nutrient absorption, fulvic acid combats vitamin and mineral deficiencies. Fulvic acid includes these nutrients 17 vitamins, 59 minerals, 12 amino acids and three essential fatty acids essential for proper cell and body development. It improves absorption of nutrients from the digestive tract into the bloodstream. Improved digestion includes gastrointestinal disorders, diarrhea, constipation, bloating, and flatulence. Fulvic acid also aids with increased energy flow, and boosts immune response. Fulvic acid is also known to be alkaline, this restores the body's optimal pH levels to improve the body's defenses against disease-causing microbes and toxins as well. Fulvic acid contributes to healthy skin, hair, and nails. Fulvic acid is a rich source of potent antioxidant, nutraceuticals, contains potent anti-inflammatory properties, aids in removal of toxins, promotes brain health and encourages muscle repair of one embodiment.

Figure 20A:
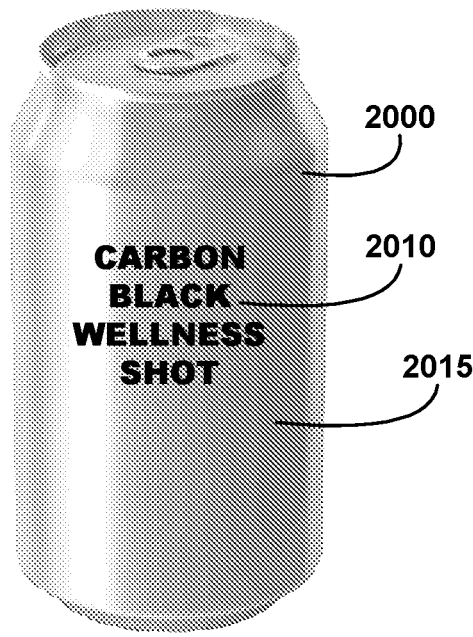
FIG. 20A shows for illustrative purposes only an example of an aluminum can carbon black wellness shot of one embodiment.

Aluminum Can Carbon Black Wellness Shot:

FIG. 20A shows for illustrative purposes only an example of an aluminum can carbon black wellness shot of one embodiment. FIG. 20A shows an aluminum pop tab can 2000 used in one embodiment to contain the carbon black wellness shot. An apparatus is used for forming and containerizing a beverage using the magnetically aligned final carbon combined compound with the carbon molecules including molecules of vitamins, mineral compounds, vitamin-like nutrients and factors and fulvic acid.

The aluminum pop tab can 2000 may be filled with carbon black wellness beverage 2015 of suspended carbon ingredients of the magnetically aligned combinations of carbon and molecules of vitamins, mineral compounds, vitamin-like nutrients and factors and fulvic acid. The light tone of the outer surface of the aluminum can is used for printing a carbon black wellness shot label in black 2010 of one embodiment.

Figure 20B:
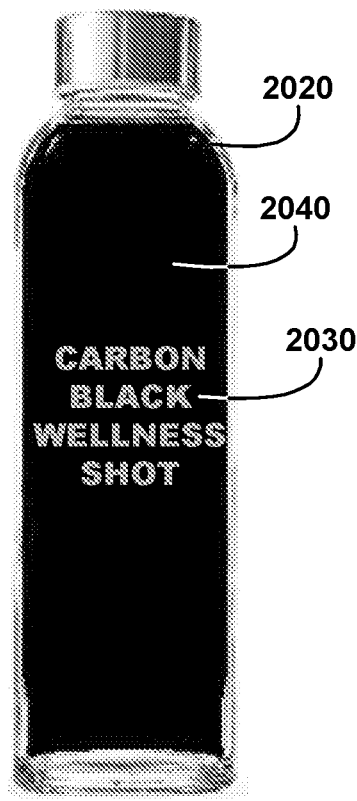
FIG. 20B shows for illustrative purposes only an example of clear glass bottle carbon black wellness shot of one embodiment.

Clear Glass Bottle Carbon Black Wellness Shot:

FIG. 20B shows for illustrative purposes only an example of clear glass bottle carbon black wellness shot of one embodiment. FIG. 20B shows a clear glass beverage bottle 2020. An apparatus is used for forming and containerizing a beverage using the magnetically aligned final carbon combined compound with the carbon molecules including molecules of vitamins, mineral compounds, vitamin-like nutrients and factors and fulvic acid.

The clear glass beverage bottle 2020 may be used as a beverage container filled with carbon black wellness beverage 2040 of suspended carbon ingredients of the magnetically aligned combinations of carbon and molecules of vitamins, mineral compounds, vitamin-like nutrients and factors and fulvic acid. Labeling the clear glass beverage bottle 2020 may be performed by printing on the clear glass surface a carbon black wellness shot label in contrasting grey 2030. The grey color will contrast with the black color of the carbon black wellness shot liquid of one embodiment.

An Example of an Application:

FIGS. 21A through 23 illustrate an example of an application of the carbon hooks compound bonding method and apparatus used for facilitating carbon bonding for lipid molecules structures used in forming liposomes. Some lipid molecule structures may include only a single long chain. In some lipid molecule structures long carbon chains may not be long enough to form a liposome encapsulation structure.

Figure 21A:
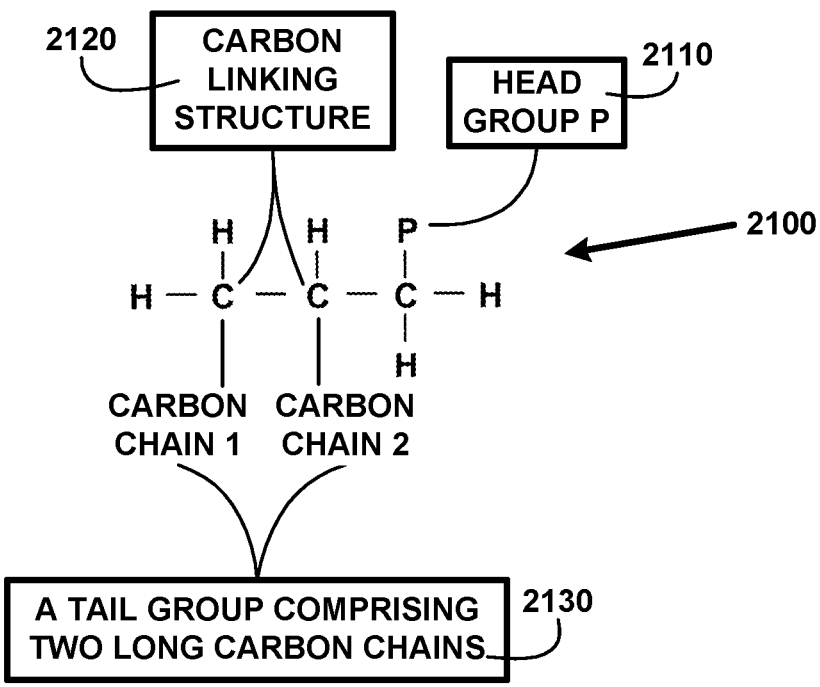
FIG. 21A shows for illustrative purposes only an example of a group of lipid molecules of one embodiment.

Group of Lipid Molecules:

FIG. 21A shows for illustrative purposes only an example of a group of lipid molecules of one embodiment. FIG. 21A shows a group of related lipid molecules 2100 of the invention may be characterized by specific structural characteristics. The structural characteristics include a head group P 2110, a carbon linking structure 2120, and a tail group comprising two long carbon chains, carbon chain 1 and carbon chain 2 2130. Not all lipid structures conform to the specific structural characteristics of one embodiment.

Figure 21B:
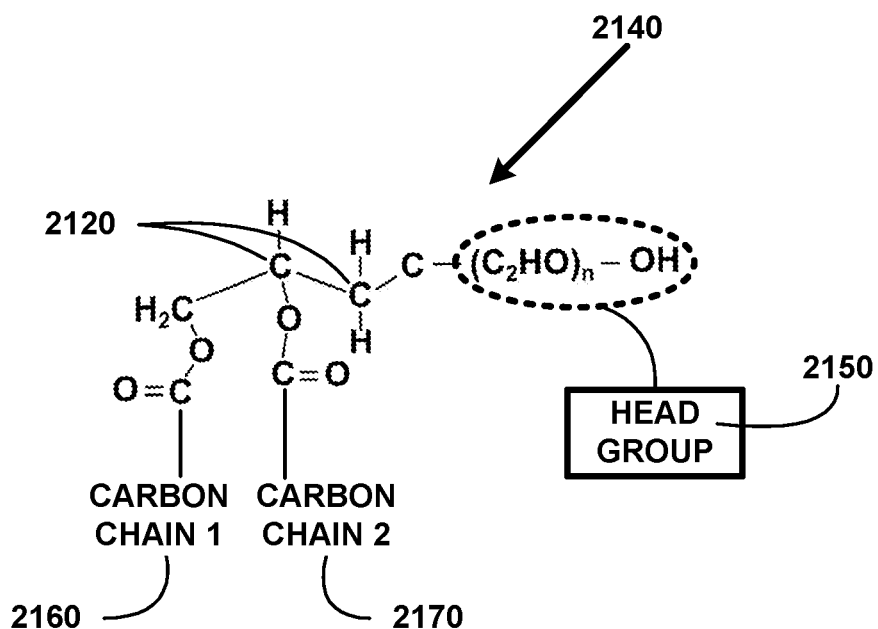
FIG. 21B shows for illustrative purposes only an example of a lipid molecule of a group of related lipids of one embodiment.

Related Lipids:

FIG. 21B shows for illustrative purposes only an example of a lipid molecule of a group of related lipids of one embodiment. FIG. 21B shows a lipid generic structural configuration described by a generic formula 2140. For example, the length of a head group 2150 may range from 12 to 45 units in length. The size of the head group may be altered by varying the size of the P chain adding additional carbon bonds. The length of carbon chain 1 2160 and carbon chain 2 2170 may range from 10 to 17 carbons in length. The length of the long carbon chains may be increased adding additional carbon bonds. In this example the illustration will show the lengthening of the long carbon chains, while an adjustment of the size of the head group and length of a carbon linking structure 2120 may also follow the same processes of the carbon hooks compound bonding method and apparatus of one embodiment.

Figures 22A, 22B, 22C:
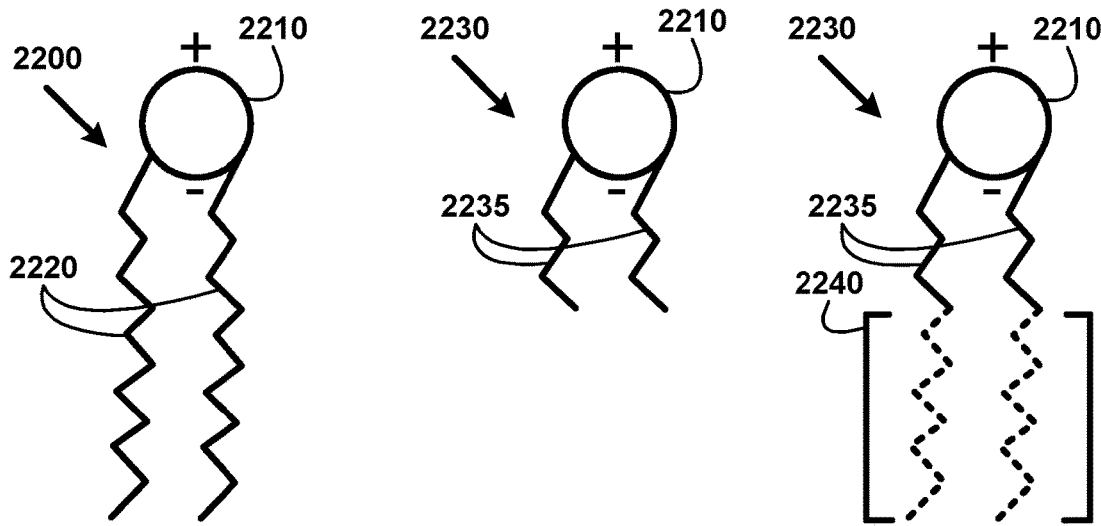
FIG. 22A shows for illustrative purposes only an example of a generic lipid molecule structure of one embodiment.
FIG. 22B shows for illustrative purposes only an example of a deficient lipid molecule structure of one embodiment.
FIG. 22C shows for illustrative purposes only an example of a planned structural extension of one embodiment.

Generic Lipid Molecule Structure:

FIG. 22A shows for illustrative purposes only an example of a generic lipid molecule structure of one embodiment. FIG. 22A shows a generic lipid molecule 2200 that includes a polar head group 2210 and a non-polar tail 2220. The generic lipid molecule 2200 has long carbon tails that allow the liposome structure to form its spherical shape of one embodiment.

Deficient Lipid Molecule Structure:

FIG. 22B shows for illustrative purposes only an example of a deficient lipid molecule structure of one embodiment. FIG. 22B shows a deficient lipid molecule 2230 that includes a polar head group 2210 and a short non-polar tail 2235. The short non-polar tail 2235 does not allow the liposome structure to form its spherical shape of one embodiment.

Planned Structural Extension:

FIG. 22C shows for illustrative purposes only an example of a planned structural extension of one embodiment. FIG. 22C shows the polar head group 2210 of the deficient lipid molecule 2230. Also showing are both of the short non-polar tail 2235 and a planned structural extension of the two short non-polar tails 2240 of the deficient lipid molecule 2230 of one embodiment.

Figure 22D:
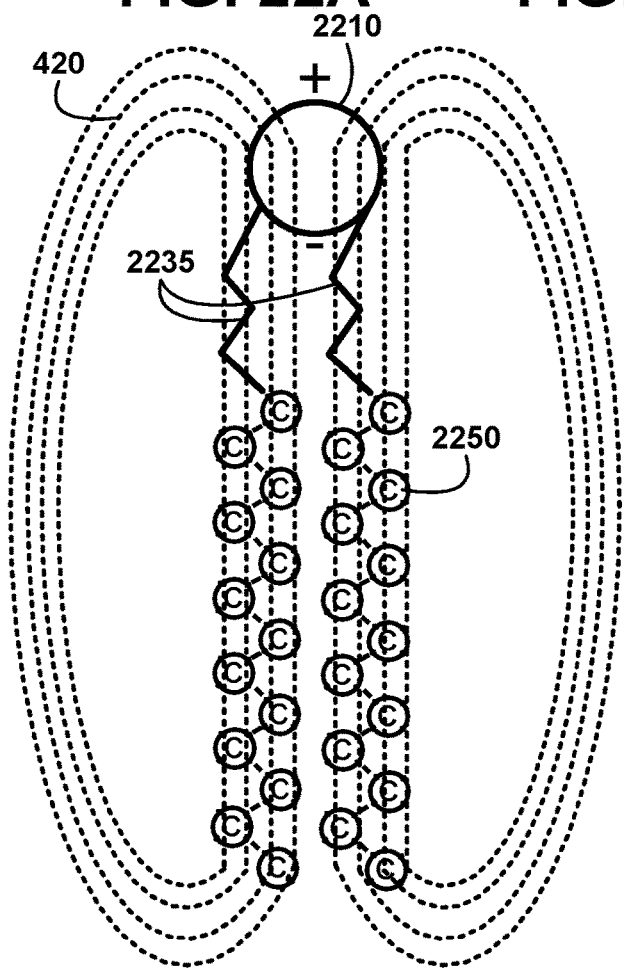
FIG. 22D shows for illustrative purposes only an example of an aligned carbon molecule bonding structural extension of one embodiment.

Aligned Carbon Molecule Bonding Structural Extension:

FIG. 22D shows for illustrative purposes only an example of an aligned carbon molecule bonding structural extension of one embodiment. FIG. 22D shows the polar head group 2210 and both of the short non-polar tail 2235. The magnetic lines of force 420 is applied to the deficient lipid molecule 2230 of FIG. 22B to align the molecule according to the polarity of the polar head group 2210. In this example a single molecule is being shown for clarity but the process includes a plurality of the deficient lipid molecule 2230 of FIG. 22B.

A plurality of a carbon molecule is added to the aligned suspended deficient lipid molecule 2230 of FIG. 22B. The carbon molecules bond to the terminus carbon molecule of the short chain and continue to bond. The shape and expanse of the magnetic domain around the deficient lipid molecule 2230 of FIG. 22B can be regulated by adjusting the power level being conducted into the electromagnets being used to create the magnetic lines of force 420. The greater the power level the farther the magnetic force expands the magnetic-domain. The distance of the magnetic domain the further the carbon chain bonding extends. This allows a predetermined number of carbon molecules to be added to the short chains to reach a tail chain length that does allow formation for the liposome spherical structure. The power level is regulated using the data from the planned structural extension to perform the aligned carbon molecule bonding structural extension of one embodiment.

Figure 22E:
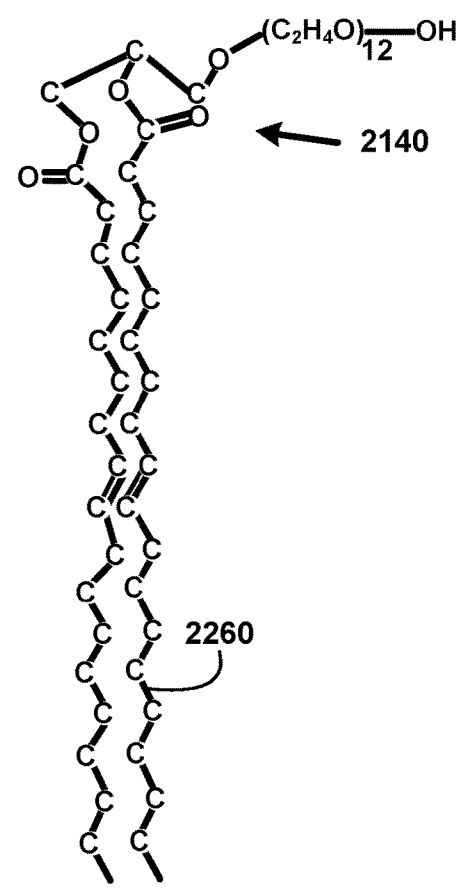
FIG. 22E shows for illustrative purposes only an example of a planned structural extension of one embodiment.

Planned Structural Extension:

FIG. 22E shows for illustrative purposes only an example of a planned structural extension of one embodiment. FIG. 22E shows the generic formula 2140 of the lipid molecule now completed through the process of the carbon hooks compound bonding method and apparatus to accomplish the planned structural extension of the two short non-polar tails 2240 to create a non-polar tail extended molecular structure 2260 of one embodiment.

Figure 23:
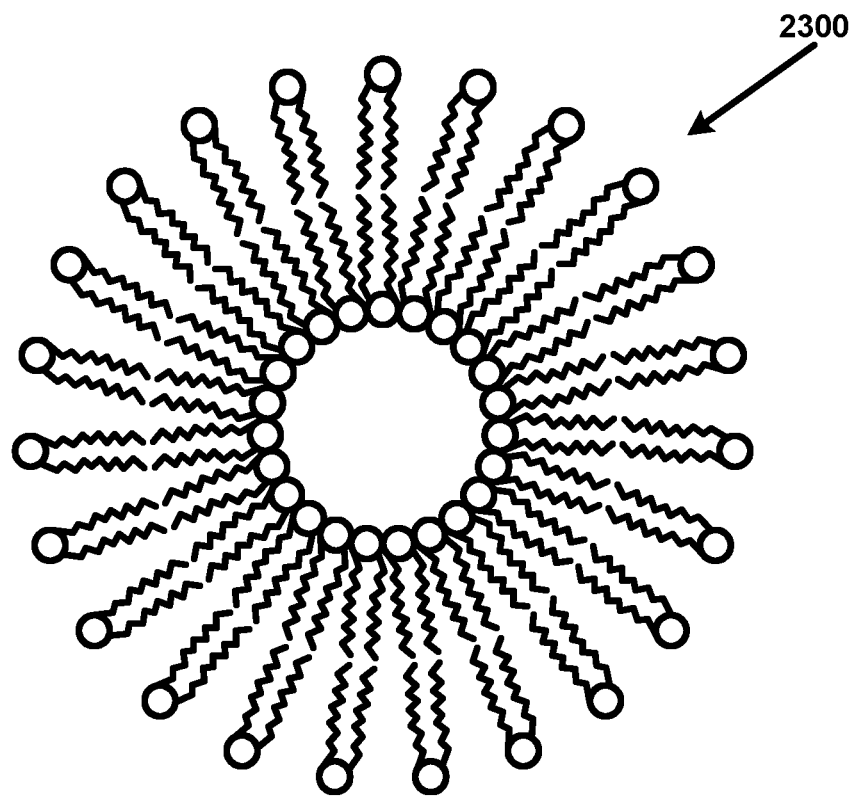
FIG. 23 shows for illustrative purposes only an example of a liposome spherical structure shown in 2D of one embodiment.

Liposome Spherical Structure Shown in 2D:

FIG. 23 shows for illustrative purposes only an example of a liposome spherical structure shown in 2D of one embodiment. FIG. 23 shows the liposome spherical structure shown in 2D 2300 formed from the extension of the carbon chains of the deficient lipid molecule 2230 of FIG. 22B of one embodiment.

Figure 24A:
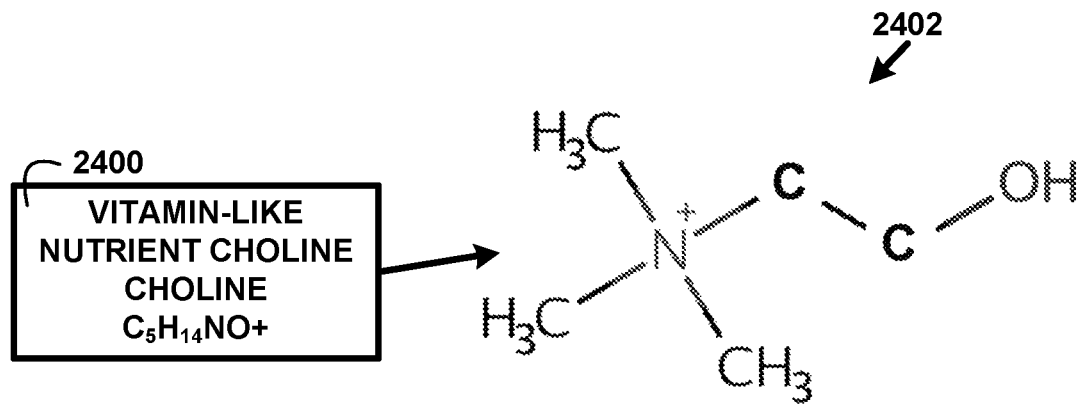
FIG. 24A shows for illustrative purposes only an example of a vitamin-like nutrient choline of one embodiment.

Vitamin-Like Nutrient Choline:

FIG. 24A shows for illustrative purposes only an example of a vitamin-like nutrient choline of one embodiment. FIG. 24A shows a vitamin-like nutrient choline. The chemical formula for choline is $C_5H_{14}NO+$ 2400. Also shown is the molecular structure for choline 2402 of one embodiment.

Figure 24B:
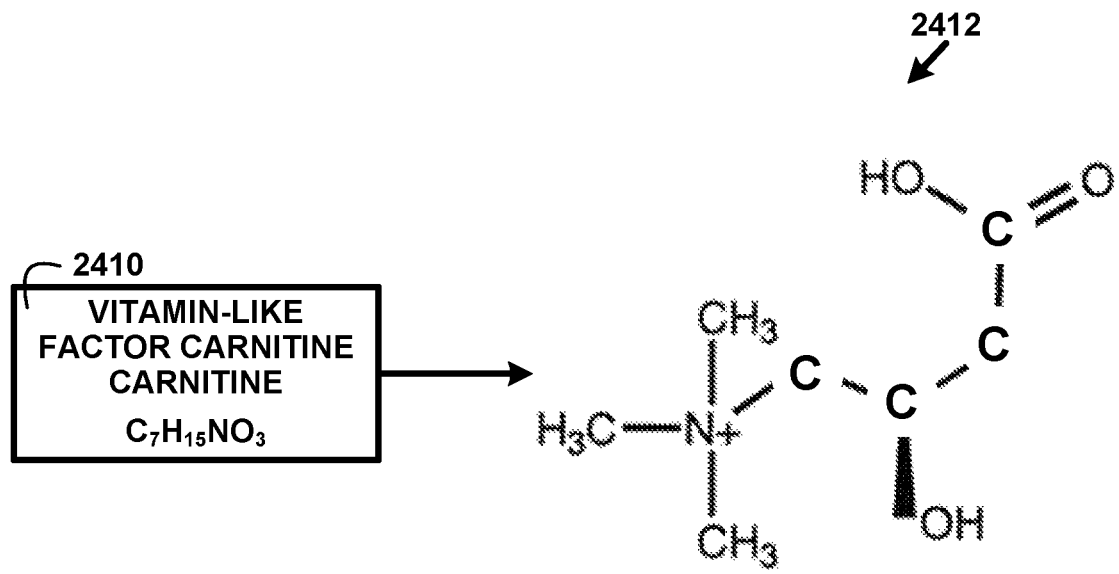
FIG. 24B shows for illustrative purposes only an example of a vitamin-like factor carnitine of one embodiment.

Vitamin-Like Factor Carnitine:

FIG. 24B shows for illustrative purposes only an example of a vitamin-like factor carnitine of one embodiment. FIG. 24B shows a vitamin-like factor carnitine. The chemical formula for carnitine is $C_7H_{15}NO_3$ 2410. Also shown is the molecular structure for carnitine 2412 of one embodiment.

The foregoing has described the principles, embodiments and modes of operation of the present invention. However, the invention should not be construed as being limited to the particular embodiments discussed. The above described embodiments should be regarded as illustrative rather than restrictive, and it should be appreciated that variations may be made in those embodiments by workers skilled in the art without departing from the scope of the present invention as defined by the following claims.

What is claimed is:

1. A method, comprising:
   providing a mixture that has nutraceutical supplement ingredients including vitamins, minerals, and trace minerals comprising trace amounts of at least chromium, copper, fluoride, iodine, iron, manganese, molybdenum, selenium and zinc;
   providing fulvic acid nutraceutical supplement ingredients with molecular structures based on a plurality of functional carbon chains and rings and amino acids and fatty acids;
   providing a black colored additive, wherein the black color is derived from the suspended carbon ingredients; and
   wherein the mixture includes water to dissolve the nutraceutical supplement ingredients in the water which forms a black colored nutraceutical supplement shot beverage mixture for human consumption.

2. The method of claim 1, wherein the nutraceutical supplement ingredients include carbon rings.

3. The method of claim 2, wherein the water ingredient is purified drinking water.

4. The method of claim 1, wherein the vitamins include at least one vitamin selected from the group of vitamins consisting of A, B1, B2, B3, B5, B-6, B7, B9, B-12, C, D, E, and K.

5. The method of claim 1, wherein the minerals include at least one mineral selected from the group of minerals consisting of chlorine, cobalt, copper, fluorine, magnesium, phosphorus, potassium, sodium, sulfur and zinc.

6. The method of claim 1, further comprising providing a flavored smoothie by mixing fruit with the black colored nutraceutical supplement shot mixture.

7. The method of claim 1, wherein the nutraceutical supplement ingredients include fulvic acid, wherein fulvic acid is water soluble at all pH levels.

8. The method of claim 1, wherein the black colored nutraceutical supplement shot mixture includes an additive ingredient which forms a black colored nutraceutical supplement shot syrup for mixing with fruit smoothies.

9. The method of claim 1, wherein the nutraceutical supplement ingredients include flavorings to form a flavored black colored nutraceutical supplement shot mixture.

10. The method of claim 1, wherein the vitamins are essential vitamins and the minerals are trace minerals, including fulvic acid.

11. A black colored nutritional supplement shot mixture, comprising:
   potable water suitable for human consumption;
   a fulvic acid nutritional supplement ingredient with molecular structures based on a plurality of functional carbon chains and rings and amino acids and fatty acids;
   a black colored additive, wherein the black color is derived from the suspended carbon ingredients; and
   a plurality of ingredients consisting of vitamins, minerals, and trace minerals comprising trace amounts of at least chromium, copper, fluoride, iodine, iron, manganese, molybdenum, selenium and zinc derived from fulvic acid, and fulvic acid dissolved in the potable water which forms the black colored nutritional supplement shot beverage mixture for human consumption.

12. The black colored nutritional supplement shot mixture of claim 11, wherein the vitamins are essential vitamins and the minerals are trace minerals, including fulvic acid.

13. The black colored nutritional supplement shot mixture of claim 11, wherein the plurality of ingredients include flavorings to form a flavored black colored nutritional supplement shot mixture.

14. The black colored nutritional supplement shot mixture of claim 11, wherein the plurality of ingredients vitamins include at least one vitamin selected from the group of vitamins consisting of A, B1, B2, B3, B5, B-6, B7, B9, B-12, C, D, E, and K.

15. The black colored nutritional supplement shot mixture of claim 11, wherein the plurality of ingredients minerals include at least one mineral selected from the group of minerals consisting of chlorine, cobalt, copper, fluorine, magnesium, phosphorus, potassium, sodium, sulfur and zinc.

16. A drinkable nutraceutical supplement shot, comprising:
   purified drinking water;
   a fulvic acid nutritional supplement ingredient with molecular structures based on a plurality of functional carbon chains and rings and amino acids and fatty acids;
   a black colored additive, wherein the black color is derived from the suspended carbon ingredients;
   at least one flavoring suitable for human consumption; and
   a plurality of supplement ingredients including vitamins, minerals, and trace minerals comprising trace amounts of at least chromium, copper, fluoride, iodine, iron, manganese, molybdenum, selenium and zinc, and fulvic acid dissolved in the purified water and the flavoring which forms a black colored drinkable flavored supplement shot beverage for human consumption.

17. The drinkable nutraceutical supplement shot of claim 16, wherein the plurality of supplement ingredients vitamins include at least one vitamin selected from the group of vitamins consisting of A, B1, B2, B3, B5, B-6, B7, B9, B-12, C, D, E, and K.

18. The drinkable nutraceutical supplement shot of claim 16, wherein the plurality of supplement ingredients minerals include at least one mineral selected from the group of minerals consisting of chlorine, cobalt, copper, fluorine, magnesium, phosphorus, potassium, sodium, sulfur and zinc.

19. The drinkable nutraceutical supplement shot of claim 16, wherein the at least one flavoring may include at least one fresh fruit.

20. The drinkable nutraceutical supplement shot of claim 16, wherein the at least one flavoring includes at least one fresh fruit mixed with the drinkable nutraceutical supplement shot mixture which forms a drinkable nutraceutical supplement shot fresh fruit flavored smoothie for human consumption.

* * * * *